US011220540B2

United States Patent
Maze et al.

(10) Patent No.: US 11,220,540 B2
(45) Date of Patent: *Jan. 11, 2022

(54) METHODS FOR REDUCING POST-OPERATIVE COGNITIVE DYSFUNCTION (POCD)

(71) Applicant: The Kennedy Trust for Rheumatology Research, London (GB)

(72) Inventors: Mervyn Maze, San Francisco, CA (US); Marc Feldmann, London (GB); Noccolo Terrando, San Francisco, CA (US); Mario Cibelli, London (GB); Daqing Ma, London (GB); Michael Fertleman, London (GB); Jagdeep Nanchahal, Oxford (GB)

(73) Assignee: THE KENNEDY TRUST FOR RHEUMATOLOGY RESEARCH, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/661,769

(22) Filed: Oct. 23, 2019

(65) Prior Publication Data
US 2020/0123245 A1    Apr. 23, 2020

Related U.S. Application Data

(60) Continuation of application No. 15/063,775, filed on Mar. 8, 2016, now abandoned, which is a division of application No. 13/579,555, filed as application No. PCT/GB2011/000220 on Feb. 17, 2011, now Pat. No. 9,308,254.

(60) Provisional application No. 61/305,500, filed on Feb. 17, 2010.

(51) Int. Cl.
| | |
|---|---|
| *C07K 16/24* | (2006.01) |
| *C07K 14/525* | (2006.01) |
| *A61K 39/395* | (2006.01) |
| *A61K 31/546* | (2006.01) |
| *A61K 31/713* | (2006.01) |
| *A61K 45/06* | (2006.01) |
| *C12N 15/113* | (2010.01) |
| *A61K 39/00* | (2006.01) |

(52) U.S. Cl.
CPC .......... *C07K 16/241* (2013.01); *A61K 31/546* (2013.01); *A61K 31/713* (2013.01); *A61K 39/3955* (2013.01); *A61K 45/06* (2013.01); *C07K 14/525* (2013.01); *C12N 15/113* (2013.01); *A61K 2039/505* (2013.01); *A61K 2039/507* (2013.01); *C07K 2317/76* (2013.01); *C12N 2310/11* (2013.01); *C12N 2310/14* (2013.01)

(58) Field of Classification Search
CPC .... C07K 16/241; A61K 31/546; A61K 45/06; A61K 2039/507
See application file for complete search history.

(56) References Cited

U.S. PATENT DOCUMENTS

| | | | |
|---|---|---|---|
| 6,419,934 B1 | 7/2002 | Tobinick | |
| 9,308,254 B2 * | 4/2016 | Maze | ...................... A61P 25/28 |

OTHER PUBLICATIONS

Adachi O, et al., "Targeted disruption of the MyD88 gene results in loss of IL-1- and IL-18 mediated function", Immunity. 1998; 9(1): 143-50.
Allan SM et al., "Interleukin-1 and neuronal injury", Nat Rev Immunol 2005; 5(8): 624-40.
Alosi F, "Immune Function of Microglia", Glia 2001; 36(2): 165-79.
Amin AR, et al., "A novel mechanism of action of tetracyclines: effects on nitric oxide synthases", Proc Natl Acad Sci U.S.A 1996; 93: 14014-19.
Andreakos E et al., "Distinct pathways of LPS-induced NF-kappa B activation and cytokine production in human myeloid and nonmyeloid cells defined by selective utilization of MyD88 and Mal/Tl RAP", Blood 2004; 103(6): 2229-37.
Annane D, "Hippocampus: a future target for sepsis treatment" Intensive Care Med 2009: 35(4) 585-6.
Arend WP, "Interleukin 1 receptor antagonist. A new member of the interleukin 1 family", J Clin Invest 1991: 88(5): 1445-51.
Ban E et al., "Brain interleukin 1 gene expression induced by peripheral lipopolysaccharide administration", Cytokine 1992; 4(1): 48-54.
Barrientos RM et al., "Memory for context is impaired by a post context exposure injection of interleukin-1 beta into dorsal hippocampus", Behav Brain Res, 2002 1134: 291-8.
Bohnen N et al., "Early and midlife exposure to anethesia and age of onset of Alzheimer's disease", Int J Neurosci 1994; 77: 181-5.
Bolles RC and Fanselow MS, "A perceptual-defensive-recuperative model of fear and pain" Behavioral & Brain Sciences 1980; 3: 291-301.
Campbell DN et al., "A prospective randomized study of local versus general anethesia for cataract surgery", Anethesia 1993; 48: 422-8.
Capuron L et al., Attentional and mnemonic deficits associated with infectious disease in humans, Psychol Med 1999; 29: 291-7.
Chen J et al., "Neuroinflammation and disruption in working memory in aged mice after acute stimulation oftl1e peripheral innate immune system", Brain Behav Immun 2008; 22(3): 301-11.
Chowdhury N et al., "Dorsal hippocampus involvement in trace fear conditioning with long, but not short, trace intervals in mice", Behav Neuroscience 2005; 119(5): 1396-402.

(Continued)

Primary Examiner — Olga N Chernyshev
(74) Attorney, Agent, or Firm — John P. White

(57) ABSTRACT

The present invention provides method, uses and agents for preventing or reducing cognitive decline in a patient following a planned inflammatory trigger. Such planned inflammatory trigger can be a surgical procedure or chemotherapy. The invention further provides methods, uses and agents for reducing cognitive decline in a patient with a cognitive disorder, wherein said patient has been exposed to an inflammatory trigger. Pharmaceutical compositions and kits are also provided.

15 Claims, 14 Drawing Sheets

(56) References Cited

OTHER PUBLICATIONS

Figure 1:
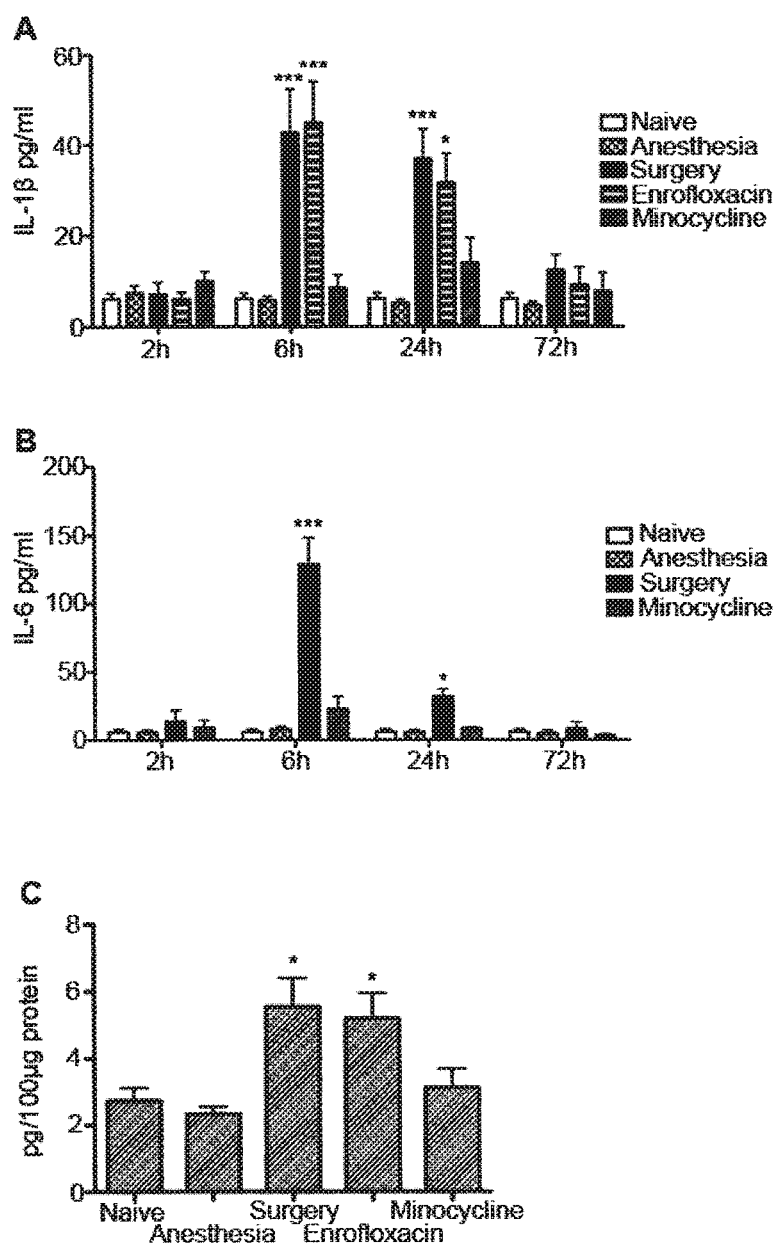

Cleren C et al., "Celastrol protects against MPTP- and 3-nitropropionic acid-induced neurotoxicity", Journal of Neurochemistry, 94 (2005), pp. 995-1004.
Colburn RW et al., "Dissociation of microglial activation and neuropathic pain behaviors following peripheral nerve injury in the rat", J. Neuroimmunol 1997; 79: 163-75.
Comery TA et al., Acute gamma-secretase inhibition improves contextual fear conditioning in the Tg2576 mouse model of Alzheimer's disease, J Neurosci 2005; 25(39): 8898-902.
Culley DJ et al., "The memory effects of general anesthesia persist for weeks in young and aged rats" Anesth Analg 2003; 96: 1004-9.
Cunningham AJ et al., "Interleukin-1 beta (IL-1 beta) and tumour necrosis factor (TNF) inhibit long-term potentiation in the rat dentate gyrus in vitro", Neurosci Left 1996; 203: 17-20.
Dantzer R, "Cytokine-induced sickness behaviour: a neuroimmune response to activation of innate immunity", Eur J. Pharmacol 2004: 500: 399-411.
Dantzer R, "How do cytokines say hello to the brain? Neural versus humoral mediation", Eur Cytokine Netw 1994; 5(3): 271-3.
Dinarello CA, "Biologic basis for interleukin-1 in disease" Blood 1996; 87: 2095-147.
Dinarello CA, "Blocking IL-1 in systemic inflammation", J Exp Med, 2005; 201(9): 1355-9.
D'Mello C et al., "Cerebral microglia recruit monocytes into the brain in response to tumor necrosis factoralpha signaling during peripheral organ inflammation", J Neurosci 2009; 29(7): 2089-102.
Du Y et al., "Minocycline prevents nigrostriatal dopaminergic neurodegeneration in the MPTP model of Parkinson's disease", Proc Nati Acad Sci USA 2001; 98: 14669-74.
Eriksson C et al., "Expression of interleukin 1 alpha and beta, and interleukin 1 receptor antagonist mRNA in the rat central nervous system after peripheral administration of lipopolysaccharides", Cytokine 2000; 12(5): 423-31.
Fan R et al., "Minocycline reduces microglial activation and improves behavioral deficits in a transgenic model of cerebral microvascular amyloid", J Neurosci 2007; 27(12): 3057-63.
Fanselow MS and Baackes MP, "Conditioned fear-induced opiate analgesia on the formalin test: Evidence for two aversive motivational systems", Learning & Motivation, 1982; 13: 200-21.
Fanselow MS, "Conditional and unconditional components of post-shock freezing", Pavlov J Biol Sci 1980; 15(4): 177-82.
Forton DM et al., "Evidence for a cerebral effect of the hepatitis C virus", Lancet 2001; 358: 38-9.
Gemma C et al., "Improvement of memory for context by inhibition of caspase-1 in aged rats" Eur J Neurosci 2005; 22(7): 1751-6.
Godbout JP et al., "Exaggerated neuroinflammation and Sickness Behaviour in aged mice following activation of the peripheral innate immune system" FASEB Journal 2005; 19: 1329-31.
Gordon SM et al., "Clinical identification of cognitive impairment in ICU survivors: insights for intensivists" Intensive Care Med 2004; 30(11): 1997-2008.
Griffin R et al., "The age-related attenuation in long-term potentiation is associated with microglial activation", J Neurochem 2006; 99: 1263-72.
Hanisch UK and Kettenmann H, "Microglia: active sensor and versatile effector cells in the normal and pathologic brain", Nat Neurosci 2007; 10(11): 1387-94.
Hansen MK et al., "Vagotomy blocks the induction of interleukin-1 beta (IL-1 beta) mRNA in the brain of rats in response to systemic IL-1 beta", J Neurosci 1998; 18(6): 2247-53.
Harry LE et al., "Comparison of the healing of open tibial fractures covered with either muscle or fasciocutaneous tissue in a murine model", J Orth Res 2008; 26: 1238-44.
Heflin LH et al., "Cancer as a risk factor for long-term cognitive deficits and dementia", J Natl Cancer Inst 2005; 97(11): 854-6.
Henry CJ et al., "Minocycline attenuates lipopolysaccharide (LPS)—induced neuroinflammation, sickness behaviour, and anhedonia", J Neuroinflamm 2008; 5: 15-29.

Hopkins RO et al., "Two-year cognitive, emotional, and quality-of-life outcomes in acute respiratory distress syndrome", Am J RespirCrit Care Med 2005; 171: 340-7.
Hoshino K et al., "Cutting edge: Toll-like receptor 4 (TLR4)—deficient mice are hyporesponsive to lipopolysaccharide: evidence for TLR4 as the Lps gene product", J Immunol 1999; 162(7): 3749-52.
International Search Report, International Application No. PCT/G2011/000220, dated Apr. 10, 2011.
Johnson T et al., "Postoperative cognitive dysfunction in middle-aged patients", Anesthesiology 2002; 96: 1351-7.
Kenny EF and O'Neill LAJ, "Signaling adaptors used by Toll-like receptors: an update", Cytokine. Sep. 2008; 43(3): 342-9.
Labow M et al., "Absence of IL-1 signaling and reduced inflammatory response in IL-1 type I receptor-deficient mice", J Immunol 1997; 159:2452-61.
Levy RM et al., "Systemic inflammation and remote organ damage following bilateral femur fracture requires Toll-like receptor 4", Am J Physiol Regul lntegr Comp Physiol. 2006; 291(4): R970-6.
Maher FO et al., "Interaction between interferon gamma and insulin-like growth factor-1 in hippocampus impacts on the ability of rats to sustain long-term potentiation", Journal of Neurochemistry 2006; 96: 1560-71.
Maier SF, et al., "The role of the vagus nerve in cytokine-to-brain communication", Ann New York Acad Sci 1998; 840: 289-300.
Marsen S et al., "Neurotoxic lesions of the dorsal hippocampus and Pavlovian fear conditioning in rats", Behav Brain Res 1997; 88(2): 261-74.
Marshall JC, Such stuff as dreams are made on: mediator-directed therapy in sepsis. Nat Rev Drug Discov 2003; 2 (5): 391-405.
Medeiros R et al., "The rold of TNF-a signaling pathway on COX-2 upregulation and cognitive decline induced by B-amyloid peptide", Behavioural Brain Research, 209, (2010), pp. 165-173.
Moje ML et al., Inflammatory blockade restores adult hippocampal neurogenesis. Science 2003; 392 (5651): 1760-5.
Moller JT et al., Long-Term postperative cognitive dysfunction in the elderly. ISPOCD 1 Study Lancet 1998; 351: 857-61.
Monk TG et al., "Predictors of cognitive dysfunction after major noncardiac surgery", Anesthesiology 2008; 108: 18-30.
Monk J.P. et al., "Assessment of Tumor Necrosis Factor Alpha Blockade as an Intervention to Improve Tolerability of Dose-Intensive Chemotherapy in Cancer Patients", Journal of Clinical Oncology, vol. 24, No. 12, (Apr. 20, 2006), pp. 1852-1859.
Morris RGM, "Synaptic plasticity and learning selective impairment of learning in rats and blockade of long-term potentiation in vivo by the N-methy-D-aspartate receptor antagonist AP5", J Neurosci 1989; 9(9): 3040-57.
Murray CA and Lynch MA, "Evidence that increase hippocampal expression of the cytokine interleukin-1 beta is a common trigger for age and stress-induced impairments in long-term potentiation", J Neurosci 1998; 18(8): 2974-81.
Newman S et al., "Postoperative cognitive dysfunction after noncardiac surgery: a systematic review", Anesthesiology 2007; 106: 572-900.
Nguyen KT et al., "Exposure to acute stress induces brain interleukin-1 beta protein in the rat", J Neurosci 1998; 18(6): 2239-46.
Nikodemova M et al., "Minocycline down-regulates MHC II expression in microglia and macrophages through inhibition of IRF-1 and protein kinase C (PKC) ALPHA.BETALL", J Biol Chem 2007; 282(20): 15208-16.
Parnet P et al., "Expression of type I and type II interleukin-1 receptors in mouse brain", Mol Brain Res 1994; 27(1): 63-70.
Pugh CR et al., "Role of interleukin-1 beta in impairment of contextual fear conditioning caused by social isolation" Behav Brain Res. 199; 106(1-2): 109-18.
Pugh CR et al., Selective effects of peripheral lipopolysaccharide administration on contextual and auditory-cue fear conditioning. Brian Behav lmmun 1998; 12: 212-29.
Pugh CR et al., The immune system and memory consolidation: a role for the cytokine IL-1 beta. Neurosci Biobehav Rev 2001; 25(1): 29-41.
Qin L et al., "Systemic LPS causes chronic neuroinflammation and progressive neurodegeneration", Gila 2007; 55(5): 453-62.

(56) References Cited

OTHER PUBLICATIONS

Riedemann NC et al., "Novel strategies for the treatment of sepsis", Nat Med 2003; 9(5): 517-24.

Rosczyk HA et al., Neuroinflammation and cognitive function in aged mice following minor surgery. Exp Gerontol 2008; 43(9): 840-6.

Skinner RA et al., "Transport of Interleukin-1 across cerebromicrovascular endothelial cells", Br J. Pharmacol 2009; 156(6): 115-23.

Tangpong, J. et al., "Adriamycin-mediated nitration of mangeanese superoxide dismutase in the central nervous system: insight into the mechanism of chemobrain", Journal of Neurochemistry, 100, (2007), pp. 191-201.

Tangpong, J. et al., "Adriamycin-induced, TNG-a-mediated central nervous system toxicity", Neurobiology of Disease, 23, (2006), pp. 127-139.

Tobinick, E., "Rapid cognitive improvement in Alzheimer's disease following perispinal etanercept administration", Journal of Neuroinflammation, vol. 5, No. 1, (Jan. 9, 2008), pp. 1-10.

Tracey D. Klareskog L et al., "Tumor necrosis factor antagonist mechanisms of action: A comprehensive review", Pharmacology & Therapeutics 2008; 117: 244-79.

Van Dam AM et al., "Immunocytochemical detection of prostaglandin E2 in microvasculature and in neurons of rat brain after administration of bacterial endotoxin", Brian Res 1993; 613(2): 331-6.

Van Rossum D and Hanisch UK, "Mircoglia" Metab Brain Dis 2004; 19(3/4) 393-411.

Van Zoelen MA et al., "Role of toll-like receptors 2 and 4, and tile receptor for advanced glycation end products in high-mobility group box 1-induced inflammation in vivo", Shock 2009; 31 (3): 280-4.

Vereker E et al., "Lipopolysaccl1aride inhibits long term potentiation in the rat dentate gyrus by activating caspase-1", J Biol Chem 2000; 274(34): 26252-8.

Wan Y et al., "Postoperative impairment of cognitive function in rats: a possible rold for cytokine-mediated inflammation in the hippocampus", Anesthesiology 2007; 106: 436-43.

Wang H et al., "HMG-1 as a alate mediator of endotoxin lethality in mice", Science 1999: 285 (5425): 248-51.

Williams-Russo P et al., "Cognitive effects after epidural vs general anesthesia in older adults: A randomized trial", JAMA 1995; 274(1): 44-50.

* cited by examiner

METHODS FOR REDUCING POST-OPERATIVE COGNITIVE DYSFUNCTION (POCD)

CROSS-REFERENCE TO RELATED APPLICATIONS

This application is a continuation of U.S. application Ser. No. 15/063,775, filed Mar. 5, 2016, which is a divisional of U.S. application Ser. No. 13/579,555, filed Nov. 21, 2012, now U.S. Pat. No. 9,308,254, issued Apr. 12, 2016, which is a § 371 national stage of PCT International Application No. PCT/GB2011/000220, filed Feb. 17, 2011, claiming the benefit of U.S. Provisional Application No. 61/305,500, filed Feb. 17, 2010, the contents of each of which are hereby incorporated by reference into the application.

The present invention relates to methods, uses and agents for preventing or reducing cognitive decline in patients following surgery or other inflammatory triggers.

Cognition, the mental activity involved in memory, attention and perception, may often decline as a result of illness (Forton et al, 2001; Hopkins et al, 2005; Helfin et al, 2005). An impairment of cognitive functions features prominently in major infective diseases (Capuron et al, 1999); the inflammatory response to infection, associated with elevated cytokines in the periphery, signals to the brain to produce an array of symptoms ranging from lethargy to social withdrawal and memory impairment, collectively known as sickness behaviour (Dantzer, 2004). The function of sickness behavior is to promote recovery from illness and injury (Bolles and Fanselow, 1980).

An impairment of cognition has also been shown to develop as a consequence of surgery (Moller et al, 1998). Termed post-operative cognitive dysfunction (POCD), it features disturbance of memory, attention, consciousness, information processing and sleep-wake cycle, leading to postoperative morbidity and mortality (Bohnen et al, 1994; Monk et al, 2008). The highest incidence of POCD occurs in elderly patients (Moller et al, 1998), but other age groups are also affected (Johnson et al, 2002).

The precise pathogenesis of POCD is not known and may involve perioperative as well as patient-related factors (Newman et al, 2007); general anesthetics have been implicated, as animal studies suggest that anesthetic-induced changes in the brain outlast the elimination of anaesthetic agents from the body (Fütterer et al, 2004) and are capable of producing long-lasting cognitive dysfunction under certain circumstances (Culley et al, 2003). Yet there appears to be no decrease in the incidence of POCD after regional anesthesia (Campbell et al, 1993; Williams-Russo et al, 1995); therefore, a causative role for general anesthetics appears to be unlikely.

Wan et al (2007) *Anaesthesiology* 106: 436-43 suggested that cognitive decline following splenectomy in adult rats is associated with a hippocampal inflammatory response that may be due to pro-inflammatory cytokine-dependent activation of glial cells.

Rosczyk et al (2008) *Exp. Gerontology* 43: 840-46 found that minor surgery leads to an exaggerated neuroinflammatory response in aged mice (compared to young mice) but that this did not result in significantly impaired performance in a memory test.

Using in vivo models of cognitive function, the present inventors have surprisingly found that ablation of interleukin-1 (IL-1) signalling and/or Tumour Necrosis Factor α (TNFα) signalling in vivo prevented surgery-induced cognitive decline.

In a first aspect, the present invention provides a method for preventing or reducing cognitive decline in a patient following a planned inflammatory trigger in said patient, the method comprising administering a therapeutically effective amount of a Tumour Necrosis Factor alpha (TNFα) antagonist to said patient.

In a second aspect, the present invention provides for the use of a therapeutically effective amount of a Tumour Necrosis Factor alpha (TNFα) antagonist in the manufacture of a medicament for use in preventing or reducing cognitive decline in a patient following a planned inflammatory trigger in said patient.

In a third aspect, the present invention provides an agent for use in preventing or reducing cognitive decline in a patient following a planned inflammatory trigger in said patient, wherein the agent comprises a therapeutically effective amount of a Tumour Necrosis Factor alpha (TNFα) antagonist.

By a "planned inflammatory trigger" we include the meaning of a planned medical procedure that may be expected to lead to an inflammatory response in the patient, and where the planned inflammatory trigger has been associated with cognitive decline in patients. Thus, this may be any procedure that has been associated with post-procedure impaired cognition, that may be for example, delirium, dementia, confusion, as defined below.

In an embodiment of the preceding aspects, the planned inflammatory trigger is surgery and the method, use or agent is thus for preventing or reducing post-operative cognitive dysfunction (POCD) in said patient.

In an alternative embodiment of the preceding aspects, the planned inflammatory trigger is chemotherapy. Delirium and other symptoms of cognitive disorders have been associated with chemotherapy treatment of cancer patients. Thus, it is envisaged that the present invention may be utilised to prevent or reduce cognitive decline in cancer patients following chemotherapy treatment, either prophylactically, or as a treatment, as described below.

By "cognitive decline" we include the meaning of any deterioration of cognitive function brought about by a cognitive disorder and/or an inflammatory trigger as defined below.

By "post-operative cognitive dysfunction", we include the deterioration of intellectual function reflected as memory and concentration impairment presenting in a patient after that patient has undergone a surgical procedure. Such deterioration of intellectual function may take many forms and as such this definition includes any form of cognitive decline presenting post-operatively. The present invention is considered to be particularly useful when administered before, during or immediately following surgery. In general, cognitive dysfunctions following surgery are common and effective immediately following recovery. Classical POCD characterises a more prolonged and subtle dysfunction in cognitive domains, juxtaposed to a more evident but short-lived "delirium" (both are included in the above definition of POCD). Discrimination between cognitive dysfunctions is made in particular according to the length of the cognitive impairment; delirium resolves itself usually after few days, whereas POCD persists for months (>3) and can become a permanent dysfunction. Thus, such cognitive decline falling within the scope of the above definition may be short-lived, thus may ablate hours or days after completion of the surgical procedure; or the cognitive decline may persist over the course of months or years, or the cognitive decline may even be permanent. Delirium is commonly seen after surgery, usually soon after surgery (hours to days) and fluctuating over time. Although the dysfunction lasts over a short period of time, delirium is associated with increased mortality (Ely et al. 2004), greater care dependency, costs (Milbrandt et al. 2004) and prolonged hospitalization (Ely et al. 2001). It is considered that the use of the present invention will aid in reducing or preventing this deterioration of intellectual function and lead to an improvement in the quality of life of the patient and his/her carers.

The diagnosis of POCD may be aided by neuropsychological testing. In general, the presence of POCD may be suspected when memory loss is greater than expected under normal situations. At present, there are no specific cognitive sets for successful POCD diagnosis; generally multiple neurocognitive assessments are made before reaching a diagnosis (Newman S et al, Anesthesiology 2007, 106(3): 572-90).

It is envisaged that the symptoms of POCD may include memory loss, memory impairment, concentration impairment, delirium, dementia, and/or sickness behaviour.

By "delirium" is included an acute and debilitating decline in attention, focus, perception, and cognition that produces an altered form of semi-consciousness. Delirium is a syndrome, or group of symptoms, caused by a disturbance in the normal functioning of the brain. The delirious patient has a reduced awareness of and responsiveness to the environment, which may be manifested as disorientation, incoherence, and memory disturbance. Delirium affects at least one in 10 hospitalised patients, and 1 in 2 elderly hospitalised patients. Whilst it is not a specific disease itself, patients with delirium usually fare worse than those with the same illness who do not have delirium. It occurs as a post-operative complication, with evidence from the mouse model described in the Examples showing that it can be caused by an inflammatory trigger. This would also explain why delirium is seen in patients admitted to hospital as a result of other inflammatory triggers, for example, stroke (CVA), Heart Attack (MI), urinary tract infection (UTI), respiratory tract infection (RTI), poisoning, alcohol or other medication withdrawal, hypoxia, and head injury.

By "dementia" we mean a serious cognitive disorder, which may be static, the result of a unique global brain injury or progressive, resulting in long-term decline in cognitive function due to damage or disease in the body beyond what might be expected from normal aging.

By "sickness behaviour" are included symptoms ranging from lethargy, fever, decreased food intake, somnolence, hyperalgesia, and general fatigue to social withdrawal and memory impairment (Dantzer R: Cytokine-induced sickness behaviour: a neuroimmune response to activation of innate immunity. *Eur J Pharmacol* 2004, 500(1-3):399-411).

The present inventors have demonstrated that microglial activation and associated inflammation are associated with the onset of POCD. Further, the ablation of microglial activation with minocycline was found to prevent post-operative memory loss in the in vivo models used. Thus, a method for assessing the onset of, or the progress of treatment for, POCD may be the analysis of microglial activation in the brain of the patient. Such activation may be measured using techniques such as Positron Emission Tomography (PET) scanning of the patient's brain. Such PET scanning may, for example, be conducted using $^{11}$C-PK11195, which is a ligand for the peripheral benzodiazepine receptor. An elevation of microglial activation may be an indication of POCD (or vice versa). Further methods of assessing POCD may include magnetic resonance imaging (MRI) or PET with FEPPA or $^{11}$C-PK11195. Other imaging techniques including MRI with diffusion tensor imaging and MR spectroscopy can also be used to non-invasively assess POCD.

Risk factors for the development of POCD include advanced age in the patient, the patient's level of education and "cognitive reserve", potential genetic polymorphisms (for example APOe4) and co-morbidities, such as underlying neurological disease.

By "preventing POCD" we include the meaning that the method, use or agent of the invention is considered to reduce the likelihood of the occurrence of POCD in a patient who has undergone a surgical procedure. Thus, the invention may be used, or be for use, prophylactically before any sign of POCD develops in the patient. While it is preferred that POCD is prevented from occurring in the patient, it is understood that some incidence of POCD may still remain but it is envisaged that the use of the present invention will reduce the symptoms of, and/or reduce the persistence of, that POCD. Thus, by "reducing POCD" we include the meaning that the onset of POCD is lessened or delayed and the symptoms are reduced thus improving the cognition of the patient while perhaps not entirely preventing the onset of the POCD. This can be established by a battery of neuropsychological tests. The invention may also be used following presentation of POCD in a patient, as a treatment for the POCD.

A further aspect of the invention provides a method for reducing cognitive decline in a patient with a cognitive disorder, wherein said patient has been exposed to an inflammatory trigger, the method comprising administering a therapeutically effective amount of a Tumour Necrosis Factor alpha (TNFα) antagonist to said patient after exposure of said patient to said inflammatory trigger.

Thus, a further aspect of the invention provides for the use of a therapeutically effective amount of a Tumour Necrosis Factor alpha (TNFα) antagonist in the manufacture of a medicament for use in reducing cognitive decline in a patient with a cognitive disorder, wherein said patient has been exposed to an inflammatory trigger.

A yet further aspect of the invention provides an agent for use in reducing cognitive decline in a patient with a cognitive disorder, wherein said patient has been exposed to an inflammatory trigger, and wherein the agent comprises a therapeutically effective amount of a Tumour Necrosis Factor alpha (TNFα) antagonist.

By "cognitive disorder" we include the meaning of any neurological disease, condition or disorder that manifests in impaired cognitive function in a patient. Such disorders may arise in patients of any age. The symptoms of such disorders may include drowsiness, fatigue, concentration impairment, vertigo, confusion, memory impairment, memory loss, delirium, loss of motor neurone control and other such symptoms as would be understood by a person of skill in the art. As explained above, delirium is a symptom, or group of symptoms, but is also a syndrome, which is caused by a disturbance in the normal functioning of the brain. Thus, it is envisaged that while delirium may be a symptom of the cognitive disorder, where another disorder is present, it may also be the only cognitive disorder that has presented in the patient and thus the present invention may be beneficial where no other cognitive disorder has yet been characterised but the patient is exhibiting signs of delirium. Further examples of cognitive disorders encompassed herein include Alzheimer's Disease, multiple sclerosis, stroke, Parkinson's Disease, Huntington's Disease, dementia, frontotemporal dementia, vascular dementia, HIV dementia, Post-Traumatic Stress Disorder and chronic inflammatory conditions such as Rheumatoid Arthritis. Further examples of relevant conditions would be known to the skilled person.

By "reducing cognitive decline" we include the meaning that the progression of the symptoms of the cognitive disorder over time is slowed and those symptoms are lessened and potentially reversed by the use of the invention. The invention may be used to improve cognitive function by reducing the onset of cognitive decline. It is hoped that such improvement may provide patients with greater independence and a greater quality of life.

By "inflammatory trigger" we include the meaning of any insult to the body that results in an inflammatory response. Such an inflammatory response, if left unchecked, may lead to an overactive neuroinflammatory response and cause or worsen (if a cognitive disorder is already present) the cognitive condition of patients. A non-exhaustive list of examples of such inflammatory triggers includes infection, trauma (such as broken bones after a fall), surgery, vaccination, arthritis, obesity, diabetes, stroke (CVA), cardiac arrest (heart attack; myocardial infarction (MI)), burns, chemotherapy, blast injury, urinary tract infection (UTI), respiratory tract infection (RTI), Human immunodeficiency virus infection (HIV), poisoning, alcohol or other medication withdrawal, hypoxia, and head injury.

It is envisaged that the patient, while potentially not already having been diagnosed with a cognitive disorder, may be at risk of developing a cognitive disorder. Thus, the present invention may also be beneficial to patients who are at risk of developing a cognitive disorder. Such patients may include the elderly or individuals who have a familial history of such disorders.

In an embodiment of the methods of the present invention, the methods may further comprise administering a therapeutically effective amount of an Interleukin 1 (IL-1) antagonist to said patient.

Thus, in an embodiment of the uses and agents of the present invention, the medicament or agent may be for administration in combination with a therapeutically effective amount of an Interleukin 1 (IL-1) antagonist.

It is envisaged that in the preceding embodiments of the invention, the IL-1 antagonist may be administered, or may be for administration, before, after or simultaneously with the TNFα antagonist. Thus, the efficacy of the invention may be improved by administering the IL-1 antagonist and the TNFα antagonist at time points where their individual efficacies may be greatest. Thus, it is envisaged that the IL-1 antagonist and the TNFα antagonist may be formulated separately.

In an alternative embodiment, the IL-1 antagonist may be co-formulated with the TNFα antagonist. Thus, in this embodiment, the administration of the IL-1 antagonist and the TNFα antagonist will be simultaneous.

In a further alternative, the IL-1 antagonist and the TNFα antagonist may be comprised in a single molecule, such as a chimeric molecule, for example, a fusion protein. Thus, a compound with both IL-1 antagonist activity and TNFα antagonist activity may be used in the methods and uses of the invention. Such compound may comprise, for example, a fusion of antigen-binding regions of antibodies with IL-1 antagonist activity and TNFα antagonist activity.

In an embodiment of any aspect of the present invention the antagonist (either IL-1 antagonist, TNFα antagonist or both) may be administered (in the methods of the invention), or may be for administration (in the uses and agents of the invention) systemically. Such systemic administration may, for example, be by intravenous (i.v.) administration in an appropriate formulation. It is envisaged that i.v. administration will lead to a rapid and more efficacious effect. An example of an embodiment where systemic administration may be appropriate includes administration to patients who are undergoing multiple surgical procedures, or where the surgical procedure results in major trauma to the body.

It is considered that the antagonists of the invention will act peripherally, but in some circumstances the agents may cross the blood:brain barrier to act directly on the brain and the central nervous system.

It is envisaged that the antagonist may be formulated as appropriate for the type of surgical procedure or cognitive disorder in question. Appropriate formulations will be evident to a person of skill in the art and may include, but are not limited to, the group comprising a liquid for injection or otherwise, an infusion, a cream, a lozenge, a gel, a lotion or a paste. The antagonist of the invention may also be for administration in biocompatible organic or inorganic matrices including, but not limited to, collagen or fibronectin matrices. It is envisaged that such matrices may act as carriers of the antagonist in an appropriate formulation or may aid in the reduction of inflammation by augmenting the effects of the antagonist.

The formulations may conveniently be presented in unit dosage form and may be prepared by any of the methods well known in the art of pharmacy. Such methods include the step of bringing into association the active ingredient (antagonist of the invention) with the carrier which constitutes one or more accessory ingredients. In general the formulations are prepared by uniformly and intimately bringing into association the active ingredient with liquid carriers or finely divided solid carriers or both, and then, if necessary, shaping the product.

In human or animal therapy, the antagonist of the invention can be administered alone but will generally be administered in admixture with a suitable pharmaceutical excipient, diluent or carrier selected with regard to the intended route of administration and standard pharmaceutical practice.

The antagonists of the invention can be administered parenterally, for example, intravenously, intra-arterially, intraperitoneally, intrathecally, intraventricularly, intrasternally, intracranially, intra-muscularly or subcutaneously, or they may be administered by infusion techniques. They may be best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose or an appropriate fraction thereof, of an active ingredient. It is preferred that doses for topical administration of the antagonists of the invention may be of the order of fractions of or multiple mg/kg body weight of the patient. For example, the dose may be between 0.01 to 500 mg/kg body weight; 1 to 400 mg/kg body weight; 2 to 200 mg/kg body weight; 3 to 100 mg/kg body weight or 4 to 50 mg/kg (or any combination of these upper and lower limits, as would be appreciated by the skilled person). The dose used may in practice be limited by the solubility of the compound. Examples of possible doses are 0.01, 0.05, 0.075, 0.1, 0.2, 0.5, 0.7, 1, 2, 5, 10, 12, 15, 20, 25, 30, 35, 40, 45, 50 or 100 mg per kg body weight up to, for example 500 mg/kg body weight, or any value in between. It is envisaged that preferred doses of antagonist would be adjusted according to relative potency. The physician or veterinary practitioner will be able to determine the required dose in a given situation based on the teaching and Examples provided herein.

Alternatively, the antagonists of the invention may be applied topically in the form of a lotion, solution, cream, ointment or dusting powder. The antagonists of the invention may also be transdermally administered, for example, by the use of a skin patch.

For application topically to the skin, the antagonists of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol, water and dimethyl sulphoxide (DMSO).

Formulations suitable for topical administration in the mouth (such as in the dental embodiments of the invention) include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

It should be understood that in addition to the ingredients particularly mentioned above the formulations of this invention may include other agents conventional in the art having regard to the type of formulation in question, for example those suitable for oral administration may include flavouring agents.

For veterinary use, a compound of the invention is administered as a suitably acceptable formulation in accordance with normal veterinary practice and the veterinary surgeon will determine the dosing regimen and route of administration which will be most appropriate for a particular animal.

In embodiments of the invention relating to preventing or reducing cognitive decline following a planned inflammatory trigger, the TNFα antagonist may be administered, or may be for administration, before, during or after the planned inflammatory trigger. For example, the TNFα antagonist may be administered, or may be for administration, before the commencement of a surgical procedure on said patient. Such administration may be immediately before surgery or several seconds, minutes or even hours before surgery. Alternatively, the TNFα antagonist may be administered, or may be for administration, during a surgical procedure on said patient.

In yet another alternative, the TNFα antagonist may be administered, or may be for administration, after completion of a surgical procedure on said patient. In this embodiment, it is envisaged that the TNFα antagonist may be administered, or may be for administration, up to 1 hour after completion of said surgical procedure. Alternatively, the TNFα antagonist may be administered, or may be for administration, between 0 seconds (i.e. immediately after completion of the surgical procedure) up to 1 day after completion of the surgical procedure. Thus this may be between 5 seconds and 10 hours after completion of the surgical procedure. Preferably, this may be between 30 seconds and 1 hour, for example 30 minutes, after completion of the surgical procedure. Such administration (or administration in any other aspect of the invention) may comprise a single administration of a single dose, or may comprise multiple administrations of the same, increasing, or decreasing doses, as appropriate. Thus, the administration may be over a course of time as prescribed by the physician.

Accordingly, the TNFα antagonist may be administered, or may be for administration to the patient; before commencement of chemotherapy; during chemotherapy; or after completion of a round of treatment of chemotherapy on said patient, when the planned inflammatory trigger is chemotherapy. The administration regimes described herein in relation to surgery also apply equally to other planned inflammatory triggers, including chemotherapy.

It is envisaged that patients who may benefit from the aspects of the invention relating to POCD may have, or be at risk of developing, delirium, Alzheimer's Disease, multiple sclerosis, stroke, Parkinson's Disease, Huntington's Disease, dementia, frontotemporal dementia, vascular dementia, HIV dementia, Post-Traumatic Stress Disorder or chronic inflammatory conditions such as Rheumatoid Arthritis.

In any aspect of the invention the patient may be a mammal. Such mammal may be a domestic pet (such as a dog or cat), a farm animal (such as a cow, pig, sheep, goat or buffalo), a sport animal (such as a horse) or a laboratory animal (such as a mouse, rat, rabbit, guinea pig, gerbil, hamster, monkey or ape). It is preferred that the patient is a human.

When the patient is a human, it is envisaged that they may be often over 50 years of age. Advanced age is a risk factor for cognitive decline and POCD thus it is envisaged that older patients may benefit more from the present invention than younger individuals. However, in a further aspect, the patient may be less than 20 years of age. Children who are born with genetic abnormalities, congenital conditions or who for any reason require surgical treatments early in life may be at risk of developing POCD and other cognitive conditions. Thus, it is also envisaged that the present invention may benefit younger patients. Nevertheless, the present invention will be useful to patients of any age who have to undergo surgical procedures for any reason and/or who may be at risk of developing a cognitive disorder.

By "TNFα antagonist" we include the meaning that the antagonist is any compound that antagonises, thus decreases or ablates, the effects of TNFα. Thus the antagonist may be a compound that targets TNFα itself, a compound that targets any upstream effector of TNFα or a compound that targets any downstream effector of TNFα. By "targeting TNFα itself" we mean blocking or reducing the transcription, translation, post-translational modification of precursors, or release of TNFα from cells where it is synthesised, as would be understood by a person of skill in the art. By "targets any upstream effector of TNFα" we mean any signal or molecule that triggers the synthesis and/or release of TNFα. By "targets any downstream effector of TNFα" we mean any receptor or other compound that interacts with TNFα to bring about its effects in vivo.

Thus, in any aspect of the invention, the TNFα antagonist may be a TNFα receptor antagonist.

The TNFα antagonist may be an antibody, an antibody fragment or fusion thereof. Thus, the TNFα antagonist may be an anti-TNFα antibody or fragment or fusion thereof. Such antibodies may be polyclonal or monoclonal. Non-human antibodies may be humanised, for use in human patients. The antibodies may alternatively be chimeric, as would be understood by a person of skill in the art. The antibody fragment may be a Fab, Fv, ScFv or dAb, as would be understood by those skilled in the art. By "ScFv molecules" we mean molecules wherein the $V_H$ and $V_L$ partner domains of the antibody are linked via a flexible oligopeptide.

The advantages of using antibody fragments, rather than whole antibodies, are several-fold. The smaller size of the fragments may lead to improved pharmacological properties, such as better penetration of solid tissue. Effector functions of whole antibodies, such as complement binding, are removed. Fab, Fv, ScFv and dAb antibody fragments can all be expressed in and secreted from *E. coli*, thus allowing the facile production of large amounts of the said fragments. Whole antibodies, and F(ab')$_2$ fragments are "bivalent". By "bivalent" we mean that the said antibodies and F(ab')$_2$ fragments have two antigen combining sites. In contrast, Fab, Fv, ScFv and dAb fragments are monovalent, having only one antigen combining site.

Many available TNFα antagonists may be useful in the context of the present invention. Agents which bind TNFα and block its action include anti human TNFα monoclonal antibodies, marketed examples include infliximab (Remicade®), adalimumab (Humira®), human TNF-R fusion protein such as etanercept (Enbrel®) or other agents which resemble antibodies which bind TNF.

Inhibitors of TNF receptor include antibodies or antibody-like molecules (fragments, chains, dAbs etc) which bind to TNF receptors, more are marketed at present.

Inhibitors of TNF signalling, and signalling pathways, include inhibitors of NFκB. MAP kinases etc. could also be used.

Alternatively, the TNFα antagonist may be a small chemical entity. Such chemical entities may be identified through high-throughput screening of compound libraries, or they may be designed in silico to interact with their intended target, such as receptors for TNFα.

In an alternative embodiment, the TNFα antagonist may be an siRNA molecule, an antisense oligonucleotide or a ribozyme. Thus, such antagonists may inhibit the transcription and/or translation of TNFα, as appropriate. Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. These nucleic acids are often termed "antisense" because they are complementary to the sense or coding strand of the gene. Recently, formation of a triple helix has proven possible where the oligonucleotide is bound to a DNA duplex. It was found that oligonucleotides could recognise sequences in the major groove of the DNA double helix. A triple helix was formed thereby. This suggests that it is possible to synthesise sequence-specific molecules which specifically bind double-stranded DNA via recognition of major groove hydrogen binding sites.

By binding to the target nucleic acid, the above oligonucleotides can inhibit the function of the target nucleic acid. This could, for example, be a result of blocking the transcription, processing, poly(A)addition, replication, translation, or promoting inhibitory mechanisms of the cells, such as promoting RNA degradations.

Antisense oligonucleotides are prepared in the laboratory and then introduced into cells, for example by microinjection or uptake from the cell culture medium into the cells, or they are expressed in cells after transfection with plasmids or retroviruses or other vectors carrying an antisense gene.

Typically, antisense oligonucleotides are 15 to 35 bases in length. For example, 20-mer oligonucleotides have been shown to inhibit the expression of the epidermal growth factor receptor mRNA (Witters et al, *Breast Cancer Res Treat* 53:41-50 (1999)) and 25-mer oligonucleotides have been shown to decrease the expression of adrenocorticotropic hormone by greater than 90% (Frankel et al, *J Neurosurg* 91:261-7 (1999)). However, it is appreciated that it may be desirable to use oligonucleotides with lengths outside this range, for example 10, 11, 12, 13, or 14 bases, or 36, 37, 38, 39 or 40 bases.

Similarly, (cf TNFα antagonist) by "IL-1 antagonist" we include the meaning that the antagonist is any compound that antagonises, thus decreases or ablates, the effects of IL-1. Thus the antagonist may be a compound that targets IL-1 itself, a compound that targets any upstream effector of IL-1 or a compound that targets any downstream effector of IL-1.

Thus, in any aspect of the present invention, the IL-1 antagonist may be an IL-1 receptor antagonist, an IL-1α antagonist, an IL-1β antagonist or a Toll-like receptor (TLR) antagonist. The IL-1 antagonist may be an antibody, an antibody fragment or fusion thereof. Thus, for example, the IL-1 antagonist may be an anti-IL-1β antibody. Alternatively, the IL-1 antagonist may be a small chemical entity. In a further alternative, the IL-1 antagonist may be an siRNA molecule, an antisense oligonucleotide or a ribozyme. In one embodiment, the IL-1 receptor antagonist is anakinra (Kineret®).

In embodiments of the invention relating to preventing or reducing cognitive decline following a planned inflammatory trigger, the IL-1 antagonist may be administered, or may be for administration, before, during or after the planned inflammatory trigger. For example, the IL-1 antagonist may be administered, or may be for administration, before the commencement of a surgical procedure on said patient. Such administration may be immediately before surgery or several seconds, minutes or even hours before surgery. Alternatively, the IL-1 antagonist may be administered, or may be for administration, during a surgical procedure on said patient.

In yet a further alternative, the IL-1 antagonist may be administered, or may be for administration, to the patient after completion of a surgical procedure on said patient. In this embodiment, it is envisaged that the IL-1 antagonist may be administered, or may be for administration, up to 1 hour after completion of said surgical procedure. Alternatively, the IL-1 antagonist may be administered, or may be for administration, between 0 seconds (i.e. immediately after completion of the surgical procedure) up to 2 days after completion of the surgical procedure. Thus this may be between 5 seconds and 1 day after completion of the surgical procedure. Preferably, this may be between 30 seconds and 10 hours, for example 2 hours, after completion of the surgical procedure. Such administration (or administration in any other aspect of the invention) may comprise a single administration of a single dose, or may comprise multiple administrations of the same, increasing, or decreasing doses, as appropriate. Thus, the administration may be over a course of time as prescribed by the physician.

Accordingly, the IL-1 antagonist may be administered, or may be for administration to the patient; before commencement of chemotherapy; during chemotherapy; or after completion of a round of treatment of chemotherapy on said patient, when the planned inflammatory trigger is chemotherapy. The administration regimes described herein in relation to surgery also apply equally to other planned inflammatory triggers, including chemotherapy.

It is envisaged that the surgical procedure in any aspect of the invention, may be a cardiothoracic, an orthopaedic, a neurological, a vascular, a plastic & reconstructive, a gynaecological, an obstetric, a urological, a general, a head & neck, an ear, nose & throat (ENT), a paediatric, a dental, a maxillofacial, an ophthalmic, a pain management, a trauma, or a minor surgical procedure. Examples of such general surgical procedure are colorectal, hepatobiliary, or upper gastro-intestinal surgical procedures. Examples of such minor surgical procedures are catheterisation, minor skin procedures, minor orthopedic procedures, nerve blocks, endoscopies, transoesophageal echocardiograms or other minor procedures.

It is envisaged that the surgical procedure may be carried out under general anaesthesia, regional anaesthesia, local anaesthesia, sedation or a combination thereof. By "general anaesthesia" is meant anaesthesia where the patient is "asleep", i.e. not conscious, during the surgical procedure. There are three phases of general anaesthesia: induction (getting off to sleep); maintenance (keeping asleep while having the surgical procedure); and emergence (waking up after the operation). Different drugs are utilised at these different stages. It is envisaged that the present invention may be suitable for application during all three phases. It is envisaged that the antagonists of the present invention may be combined with other drugs, such as anaesthetic drugs, for ease of administration during the different phases of anaesthesia, if appropriate, as would be directed by the physician.

Regional anaesthesia involves an infusion or single injection of local anaesthetic sometimes with additives (opioids, clonidine, etc) at a site away from the operative field. For example, spinal (intrathecal) anaesthesia (caesareans, prostate surgery, knee surgery), epidural anaesthesia, caudal anaesthesia, regional nerve blocks (Bier's block for the arm). The present invention may also be useful for application in surgical procedures carried out under regional anaesthesia. Antagonists of the present invention may be combined with anaesthetic formulations for ease of administration, if appropriate.

Local anaesthesia involves injection of local anaesthetic drugs close to the area where the procedure is to be carried out.

An aspect of the present invention provides a kit of parts comprising an IL-1 antagonist and a TNFα antagonist for use in preventing or reducing cognitive decline in a patient following a planned inflammatory trigger. Such planned inflammatory trigger may be a surgical procedure and the kit may therefore be for preventing or reducing post-operative cognitive dysfunction (POCD) in a patient. Alternatively, the planned inflammatory trigger may be chemotherapy. It is preferred that the IL-1 antagonist is an IL-1 receptor antagonist and the TNFα antagonist is an anti-TNFα antibody.

A yet further aspect of the invention provides a kit of parts comprising an IL-1 antagonist and a TNFα antagonist for use in reducing cognitive decline in a patient with a cognitive disorder, wherein said patient has been exposed to an inflammatory trigger. It is preferred that the IL-1 antagonist is an IL-1 receptor antagonist and the TNFα antagonist is an anti-TNFα antibody. The cognitive disorder may be as defined above.

The invention further provides a kit of parts comprising: an IL-1 antagonist; a TNFα antagonist; and instructions for administration of said IL-1 antagonist and TNFα antagonist to a patient before, during or after a planned inflammatory trigger. Such planned inflammatory trigger may be a surgical procedure or chemotherapy, for example.

A further aspect of the present invention provides a method for preventing or reducing cognitive decline in a patient following a planned inflammatory trigger in said patient, the method comprising administering a therapeutically effective amount of an Interleukin 1 (IL-1) antagonist to said patient. The planned inflammatory trigger may be surgery and the method may therefore be for preventing or reducing post-operative cognitive dysfunction (POCD). Alternatively, the planned inflammatory trigger may be chemotherapy.

The IL-1 antagonist may be administered to the patient before commencement of a surgical procedure on said patient. Alternatively, the IL-1 antagonist may be administered to the patient during a surgical procedure on said patient. In a further alternative, the IL-1 antagonist may be administered to the patient after completion of a surgical procedure on said patient. Such treatment regime applies accordingly when the planned inflammatory trigger is other than surgery, for example chemotherapy.

A further aspect provides a method for reducing cognitive decline in a patient with a cognitive disorder, wherein said patient has been exposed to an inflammatory trigger, the method comprising administering a therapeutically effective amount of an Interleukin 1 (IL-1) antagonist to said patient after exposure of said patient to said inflammatory trigger. It is envisaged that the cognitive disorder may be selected from, but not limited to, the group comprising delirium, Alzheimer's Disease, multiple sclerosis, stroke, Parkinson's Disease, Huntington's Disease, dementia, frontotemporal dementia, vascular dementia, HIV dementia, Post-Traumatic Stress Disorder or chronic inflammatory disorders such as Rheumatoid Arthritis.

The present invention further provides an antagonist of the present invention in combination with a pharmaceutically acceptable carrier.

All documents referred to herein are incorporated herein, in their entirety, by reference.

The listing or discussion of a prior-published document in this specification should not necessarily be taken as an acknowledgment that the document is part of the state of the art or is common general knowledge.

The invention is now described in more detail by reference to the following, non-limiting, Figures and Examples.

FIGURES

FIG. 1. Surgery-induced systemic inflammation is associated with increased expression of hippocampal IL-1β and is blocked by minocycline IL-1β and IL-6 levels in plasma were measured by ELISA at 2, 6, 24 or 72 hours post-intervention. Surgery resulted in increased plasma levels of IL-1β (A) and IL-6 (B) compared to mice receiving the same anesthetics without surgery (Anesthesia) or to naïve animals. Administration of minocycline (40 mg/kg, i.p.), an antibiotic with anti-inflammatory properties, mitigated surgery-induced elevations in IL-1β and IL-6 in plasma. Enrofloxacin, a comparable antimicrobial to minocycline but devoid of any anti-inflammatory properties failed to reduce plasma levels of IL-1β, compared to surgical littermates (Surgery) injected with saline (n=6). Six hours after surgery IL-1β expression in the hippocampus was increased compared to naïve and anesthesia groups (C). Administration of minocycline but not enrofloxacin mitigated surgery-induced, IL-1β-mediated, hippocampal inflammation (n=7). Data are expressed as mean±SEM, ***$p<0.001$; *$p<0.05$; for comparison between surgery or enrofloxacin vs naïve, anesthetics and minocycline groups.

Figure 2:
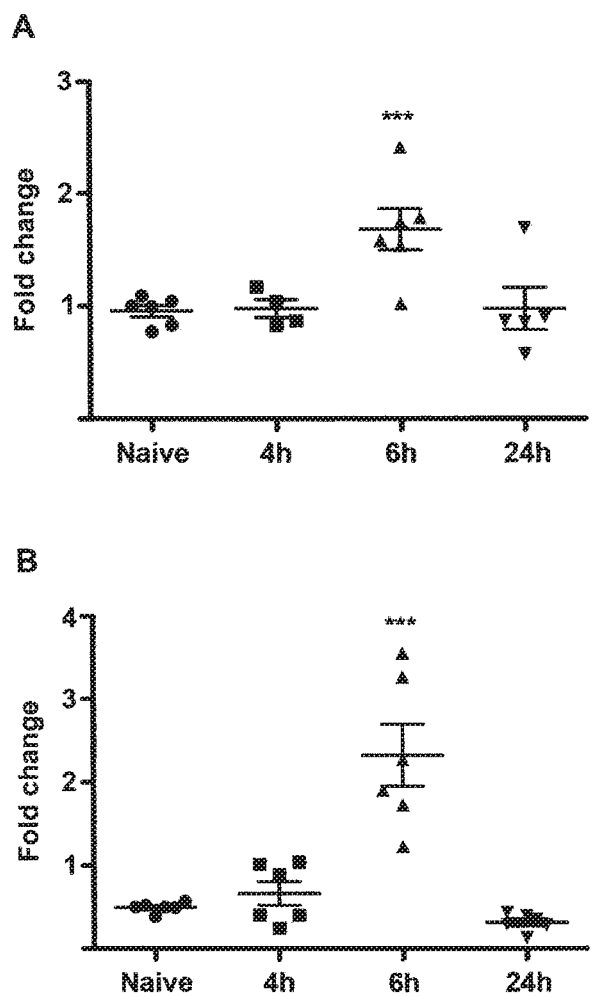

FIG. 2. Surgery induces transcription of IL-1β and IL-6 in the hippocampus. IL-1β (A) and IL-6 (B) mRNA were measured by quantitative real time PCR (qRT-PCR) in hippocampal samples extracted 4, 6 or 24 hours after surgery. Naïve animals were used as controls. Surgery resulted in increased transcription of both IL-1β and IL-6 in the hippocampus compared to naïve group, 6 hours after surgery and had returned to normal by 24 hours after surgery (n=6). Data are expressed as mean fold change ±SEM, *** $<0.001$; for comparison between surgery vs naïve group.

Figure 3:
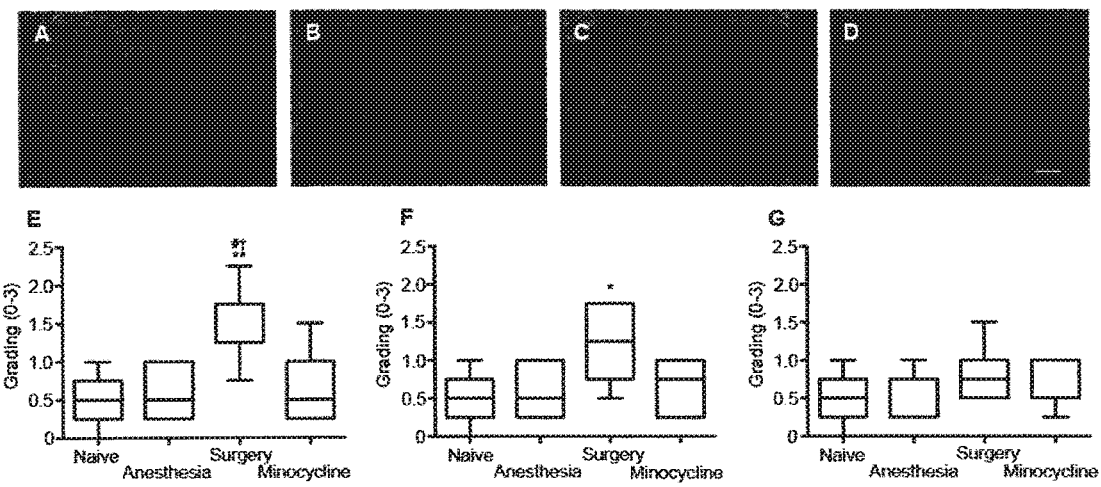

FIG. 3. Immunohistochemistry of microglia with anti-CD11b (A, B, C, D). Hippocampi were harvested 1, 3 or 7 days after treatment (pictures shown refer to tissue harvesting after 1 day) and stained with avidin-biotin technique. Representative photomicrographs from naïve (A) anesthetics alone (B) surgical (C), and surgical animals treated with minocycline (D). The amoeboid hypertrophy of cell bodies, as well as clumping of processes seen following surgery is prevented by administration of minocycline. Scale bar 30 μm. Median (horizontal bar) with 25th to 75th (box) and 10th to 90th (whiskers) percentiles for immunohistochemical grading (0-3) of microglia (E, F, G). One day after surgery mice showed significantly higher levels of reactive microgliosis compared to naive, anesthetics only or surgical mice treated with minocycline (E). Three days after surgery mice continued to show an increase in reactive microglia compared with naive animals (F). By 7 days microglial activation had returned to normal (G). **$p<0.01$ and *$p<0.05$ vs naïve animals; #$p<0.05$ vs anesthesia group; †$p<0.05$ vs minocycline group; for significant group difference, (n=7).

Figure 4:
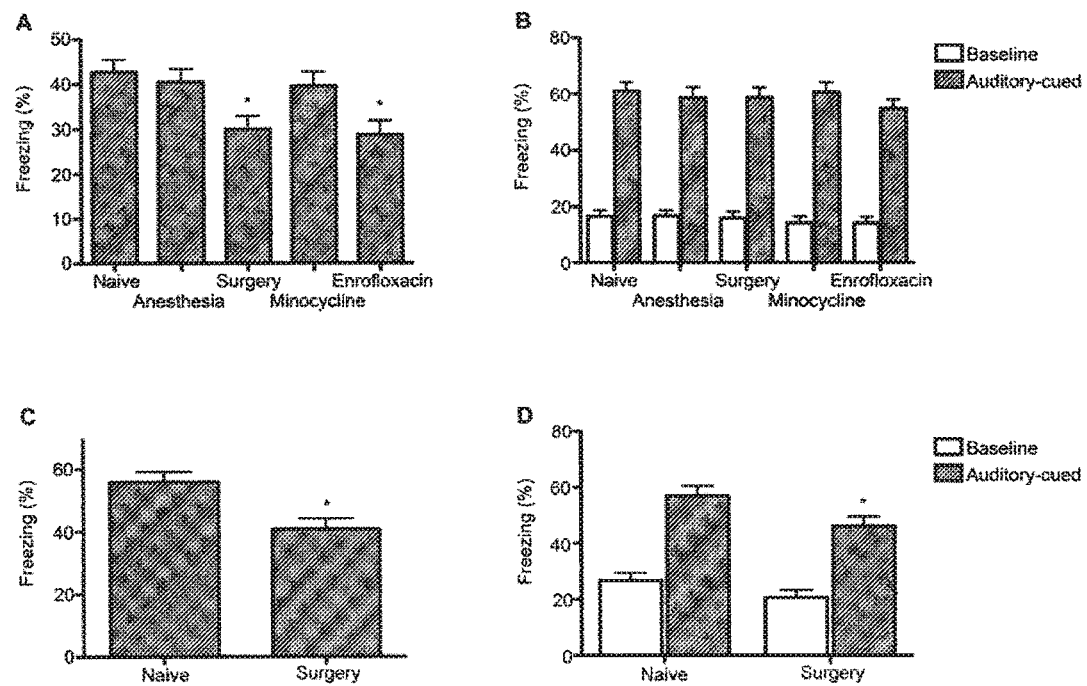

FIG. 4. Hippocampal-dependent recall of fear memories is impaired after surgery. Rodents underwent fear conditioning and 30 min later they were divided to receive anesthetics (Anesthesia), or surgery of the tibia under anesthesia (Surgery), or the same surgical procedure with minocycline (Minocycline) or enrofloxacin (Enrofloxacin) administration, respectively. Naive group received no treatment. Contextual and acoustic-cued memories were tested three days later. A. Recall of contextual delay fear conditioning memories, as measured by freezing behavior, was impaired in surgical animals compared to naïve and anesthesia groups. Administration of minocycline, but not enrofloxacin, mitigated the surgery-induced, decrement in freezing. *$p<0.05$ vs naïve, anesthesia and minocycline groups; (n=34). B. Freezing in the auditory-cued test after delay fear conditioning. There was no difference between the groups in either baseline or auditory-cued-related freezing behavior, thus suggesting that amygdalar-dependent memory function is intact after surgery. (n=34). C. Freezing to context after trace fear conditioning. Mice subjected to surgery exhibited reduced freezing to context when compared to naïve animals, confirming that the inflammation induced by surgery disrupts recall of fear contextual memories formed in the hippocampus after trace conditioning. *$p<0.05$; (n=28). D. Hippocampal-dependent, surgery-induced memory impairment is shown in the auditory-cued test, in mice trained with trace fear conditioning. There is a significant difference between the groups in auditory-cued-related freezing behavior, suggesting disruption of auditory-cued, hippocampal-dependent, retrieval of memories after surgery. No difference was shown in the baseline freezing behavior. *$p<0.05$; (n=28).

Figure 5:
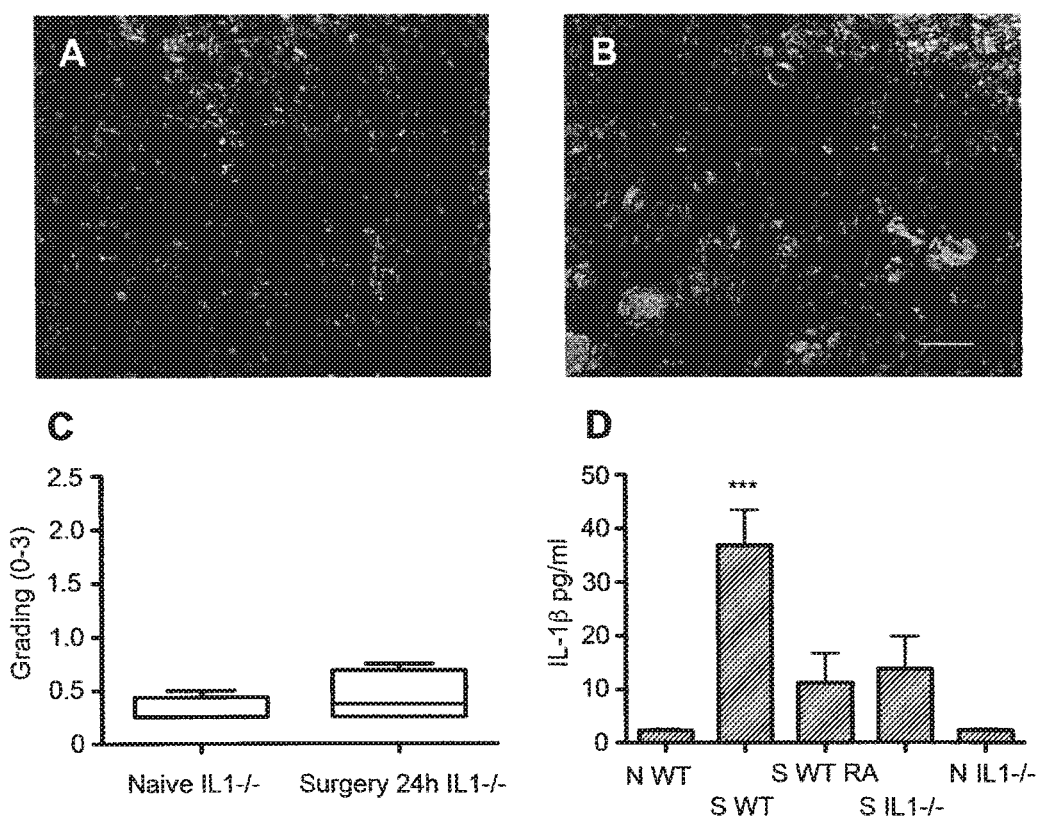

FIG. 5. Surgery-induced inflammation is mitigated in mice in which IL-1 signalling is disabled or reduced.

Immunohistochemistry of hippocampal microglia with anti-CD11b in IL1R$^{-/-}$ mice (A-B). Representative microglia from naïve (A) and surgical IL-1R$^{-/-}$ mice 24 h after surgery. Scale bar 30 μm. Box and whiskers plot of microgliosis in IL1R$^{-/-}$ mice (C). Grading of microgliosis confirms that surgery did not activate microglia in IL1R$^{-/-}$ mice, compared to naïve littermates, one day after the procedure. Circulating IL-1β in IL1R$^{-/-}$ mice and in WT pre-treated with IL-1R antagonist prior to surgery (D). Surgery did not induce a significant increase of IL-1β at 24 h in either IL1R$^{-/-}$ mice or in WT animals treated with IL-1Ra prior to surgery. Data are expressed as mean±SEM, ***$p<0.001$ vs any other group; n=6. N WT=naïve wild type; S WT=wild type undergoing surgery; S WT RA=wild type pre-treated with IL-1Ra prior to surgery; S IL1R–/–=mice lacking IL-1R undergoing surgery; N IL1R–/–=naïve mice lacking IL-1R.

Figure 6:
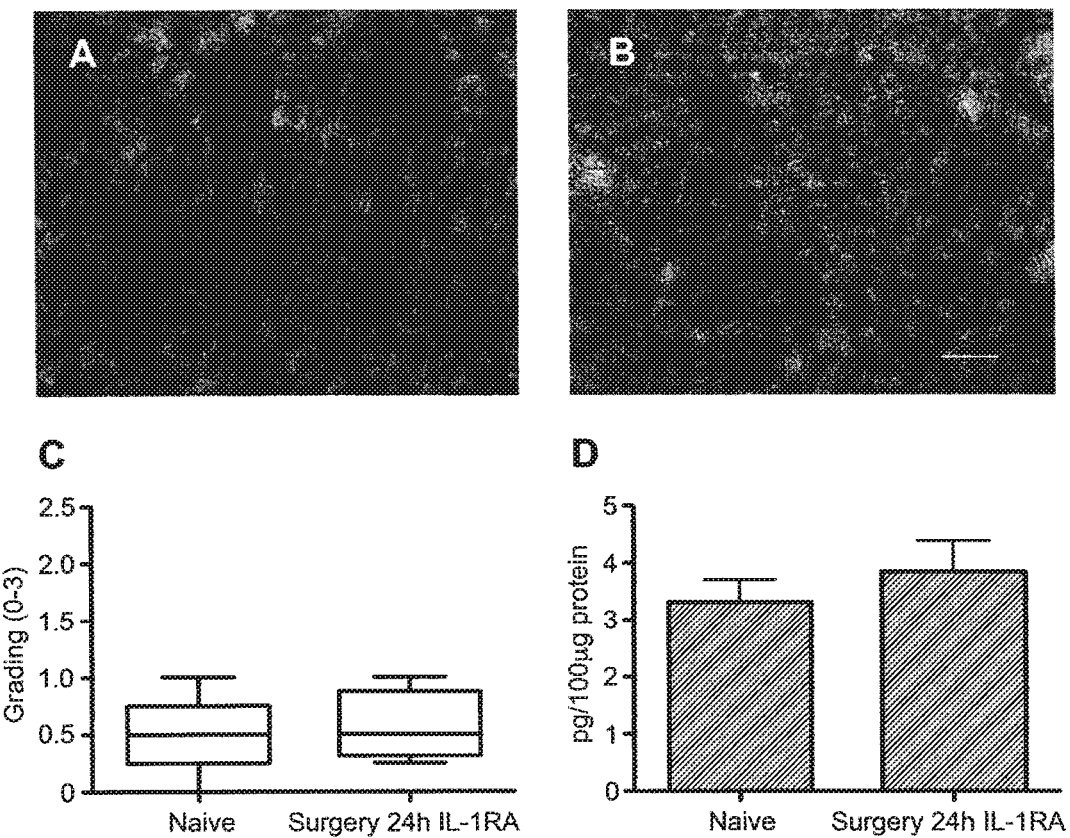

FIG. 6. IL-1 receptor antagonist (IL-1Ra) prevents hippocampal neuroinflammation after surgery.

Immunohistochemistry of hippocampal microglia with anti-CD11b in WT mice pre-treated with IL-1Ra (A-B). Representative photomicrographs from naïve (A) and surgical mice (B) pretreated with IL-1Ra. Scale bar 30 μm. Box and whiskers plot for grading of microgliosis in IL-1Ra treated surgical mice (C). Grading of microgliosis confirms that surgery did not activate microglia if IL-1Ra was given pre-operatively. Hippocampal expression of IL-1β in IL1Ra pre-treated surgical mice (D). Hippocampal IL-1β did not significantly increase in mice treated with IL-1Ra undergoing surgery compared to naïve mice. All assessments were conducted 24 hours after surgery. Data are expressed as mean±SEM; n=6.

Figure 7:
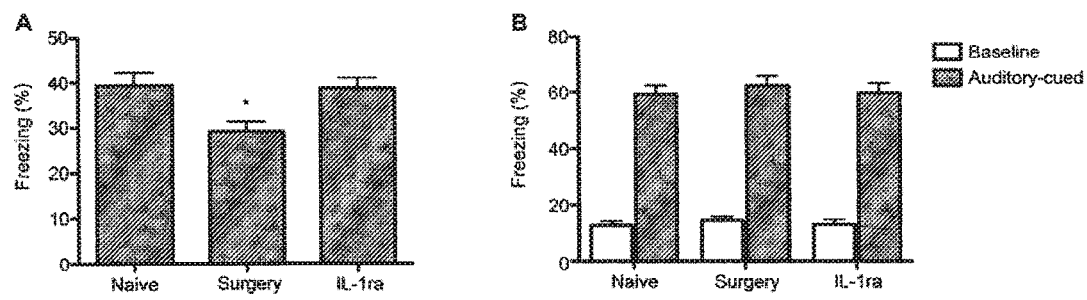

FIG. 7. Surgery-induced impairment of contextual fear memories is prevented by pre-emptive administration of IL-1 receptor antagonist (IL-1Ra). A. IL-1Ra, injected before surgery, significantly reduced the surgery-induced decrement in freezing behavior. *$p<0.05$; (n=30). B. Freezing in the auditory-cued test after delay fear conditioning. There was no difference between the groups in either baseline or auditory-cued-related freezing behavior, suggesting that neither surgery, nor IL-1Ra affected amygdalar-dependent memory function (n=30). Data are expressed as mean±SEM percentage of freezing response.

Figure 8:
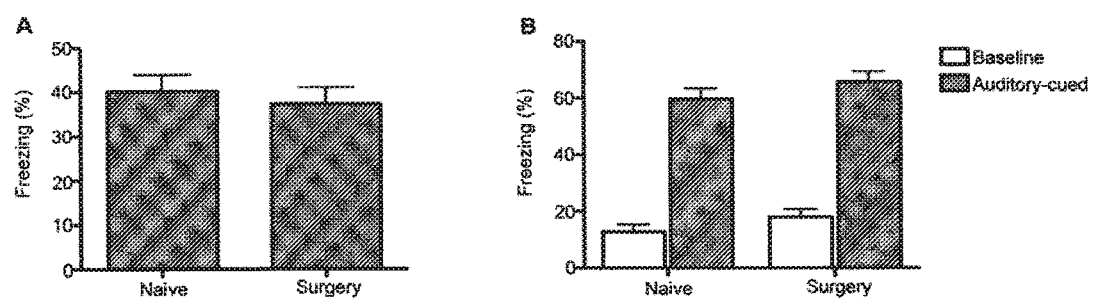

FIG. 8. Recall of contextual and auditory-cued memories is not affected if surgery is delayed three days after conditioning. A. Freezing to the context in mice undergoing surgery three days after delay fear conditioning. Surgery performed three days after treatment did not affect freezing to context when compared to naïve animals. (n=28). B. Freezing in the auditory-cued test after training with delay fear conditioning. There was no difference between the groups in either baseline or auditory-cued-related freezing behavior. (n=28).

Figure 9:
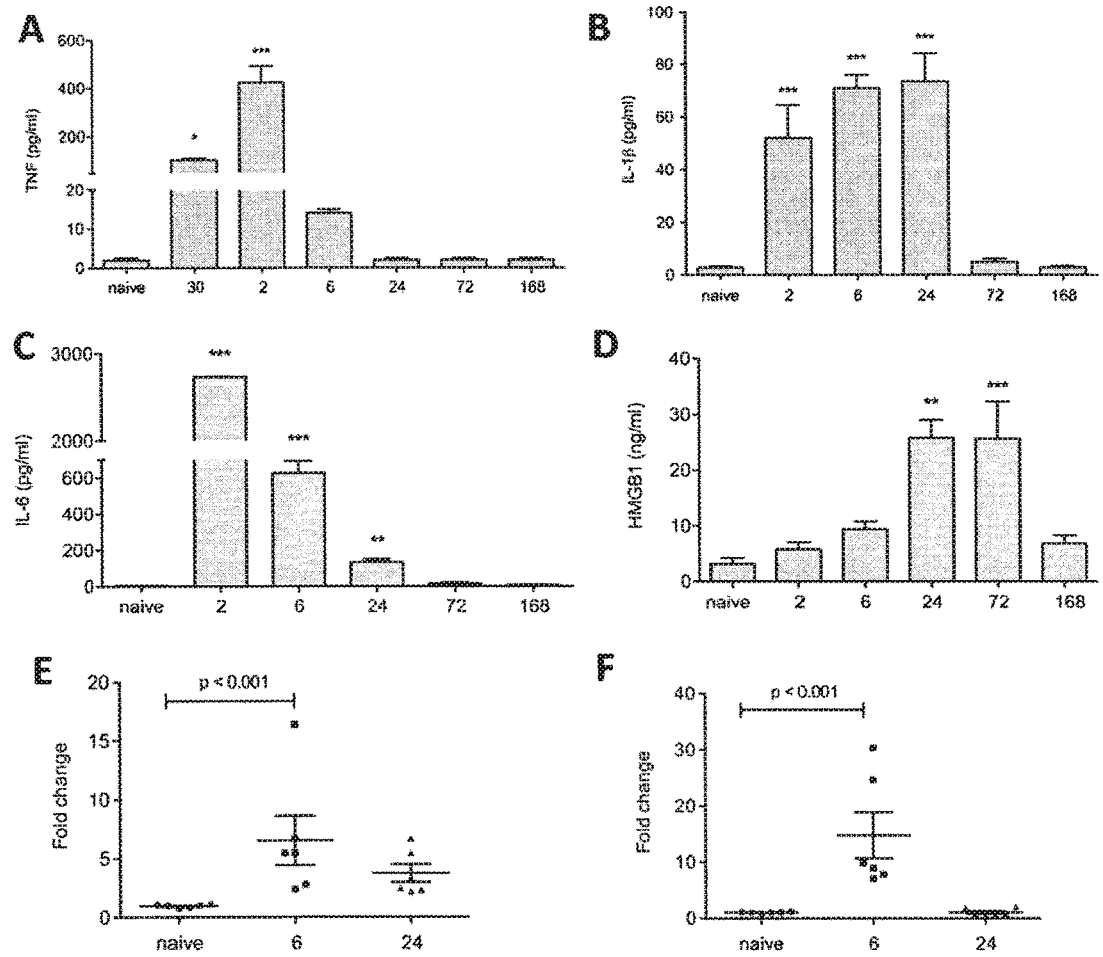

FIG. 9: Inflammatory response after LPS exposure. Mice were injected with LPS at time zero and plasma levels of TNFα, IL-1β, IL-6 and HMGB-1 were measured by ELISA. TNFα was increased after 30 minutes and peaked at 2 hours, returning to baseline thereafter (A; * p<0.01; * p<0.001 vs naïve). IL-1β was detected after 2 hours from LPS administration and levels continued to steadily increase until 24 hours (B; * p<0.001 vs naïve). IL-6 expression was highly elevated at 2 hours, decreasing at 6 hours but still significantly detectable at 24 hours compared to naïve animals (C; * p<0.0001;  p<0.001 vs naïve respectively). Levels of HMGB1 started to increase at day 1 and until day 3 (D;  p<0.001; * p<0.0001 vs naïve). Increased mRNA expression of IL-1β (E) and IL-6 (F) was found at 6 hours after peripheral LPS injection in the hippocampus of mice using qPCR (p<0.001 vs naïve); mRNA expression returned to normal by day 1. Data are expressed as mean±SEM (n=6) and compared by one-way analysis of variance and Student-Newman-Keuls method.

Figure 10:
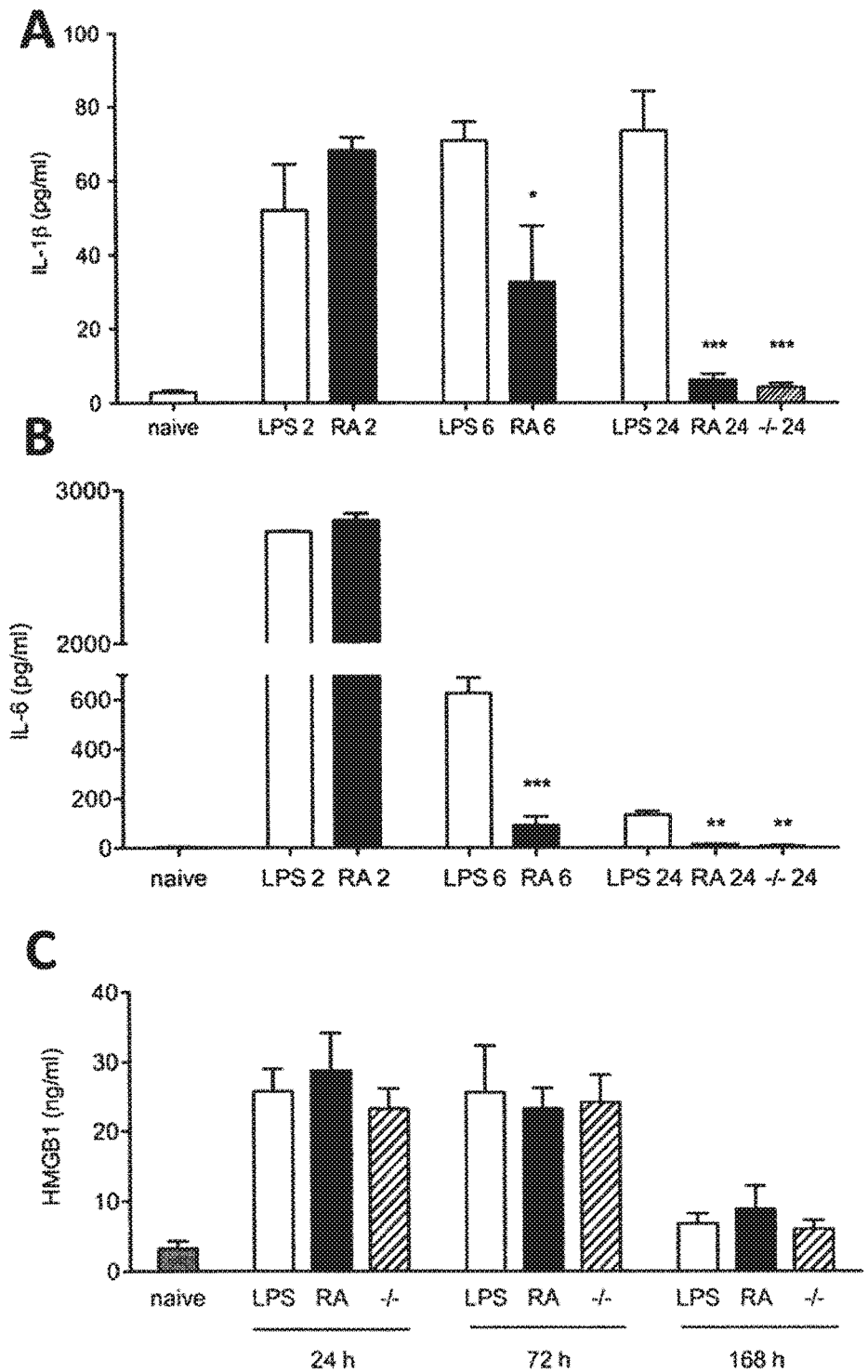

FIG. 10: Blocking IL-1 reduces systemic cytokine release. Animals received LPS (LPS) or treatment with IL-1Ra immediately before LPS exposure (RA). Plasma levels of IL-1β and IL-6 were measured by ELISA at 2, 6, and 24 hours. Pre-emptive administration of IL-1 Ra significantly reduced the amount of plasma IL-1β at 6 hours (A; * p<0.01 vs LPS) and 24 hours (* p<0.001 vs LPS). IL-6 followed a similar trend, with a strong decrease in plasma concentrates at 6 hours (B; * p<0.001 vs LPS) and at 24 hours ( p<0.001 vs LPS). To corroborate the findings, levels of IL-1β and IL-6 were measured in IL-1R$^{-/-}$ (-/-) (A-B, * p<0.0001 and** p<0.001 vs LPS respectively). IL-1Ra or IL-1R$^{-/-}$ had no effects on HMGB-1 release in plasma (C). Data are expressed as mean±SEM, (n=6) and compared by one-way and two-way (IL1R$^{-/-}$) analysis of variance and Student-Newman-Keuls method.

Figure 11:
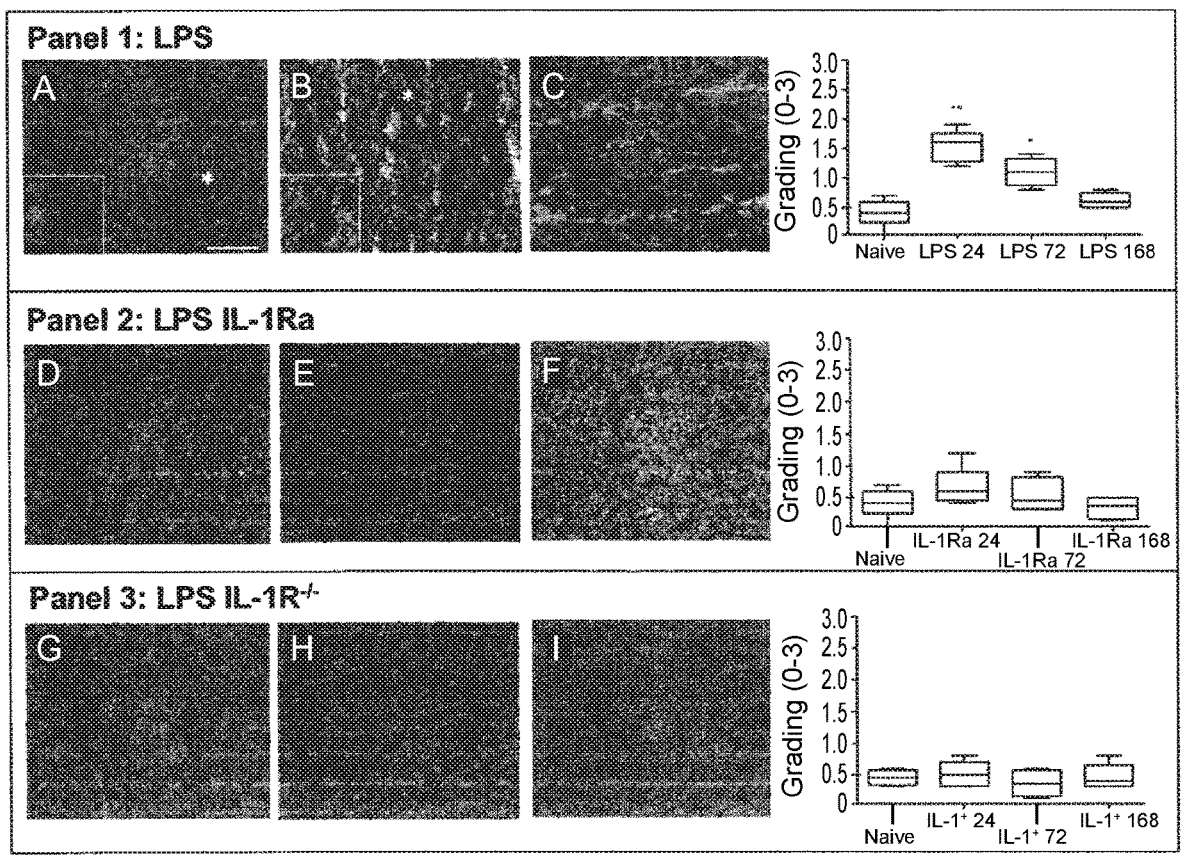

FIG. 11: Blocking IL-1 reduces microglia activation. Hippocampi were harvested at days 1, 3, 7 after LPS administration and stained with anti-CD11b. Pictures show CA1 (scale bar 50 μm, 20×) and photomicrographs were blindly scored and microglia activation was graded on a scale 0 (lowest)-3 (highest). PANEL 1: LPS. Reactive microglia were found at days 1 and 3 after LPS injection (B-C) compared to naive (A). Resting microglia (box A, 40×) shifted to a "reactive state" (box B, 40×). PANEL 2: IL-1Ra. Reduction in the number of reactive microglia was observed after administering IL-1Ra both at days 1 and 3 (E-F), with no changes from controls (D). PANEL 3: IL-1R. Administration of LPS to IL-1R$^{-/-}$ did not induce microglia activation at any time point assessed (G-H-I).

Median (horizontal bar) with 25th to 75th (box) and 10th to 90th (whiskers) percentiles for immunohistochemical grading (0-3) illustrates panels 1, 2, and 3. One day after LPS administration we found clear microgliosis, which was attenuated by IL-1Ra treatment (day 1 ** p<0.001 vs naïve, day 3 * p<0.05 vs naïve). Significant reduction in microgliosis was found both after IL-1 Ra administration and in IL-1R$^{-/-}$ (n=4). Non parametric data are presented with Kruskal-Wallis followed by Dunn's test.

Figure 12:
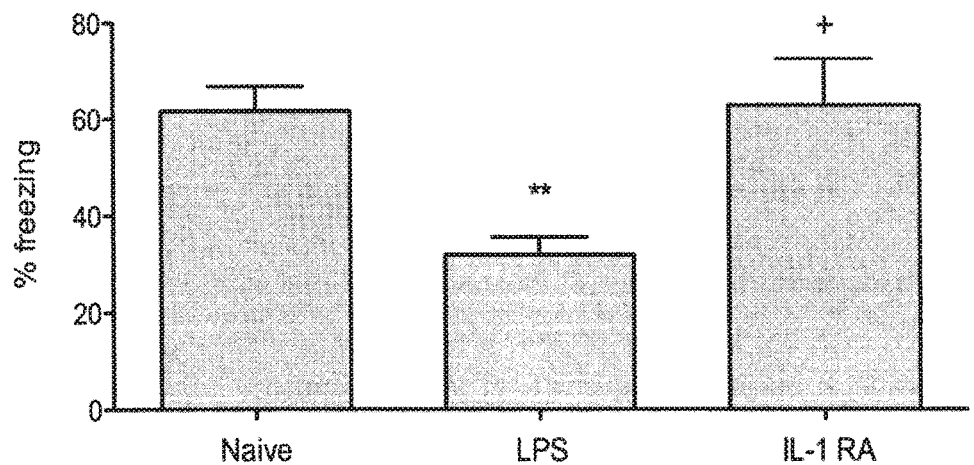

FIG. 12: Contextual fear response is ameliorated by pre-emptive IL-1 Ra. Within thirty minutes following training, mice were injected with LPS. Three days later, rodents were exposed to the same context in which fear conditioning was previously carried out. Contextual fear response reveals a clear hippocampal-dependent memory impairment (A, ** p<0.005 vs naive). Pre-treatment with IL-1Ra abolished the main symptoms of sickness behavior and significantly ameliorated the memory retention at day 3 (A, * p<0.05 vs LPS). The auditory-cued test did not show any difference between groups or in baseline freezing (B). Data are expressed as mean±SEM (n=9 for acute behavior) and compared by one-way analysis of variance and Student-Newman-Keuls method.

Figure 13:
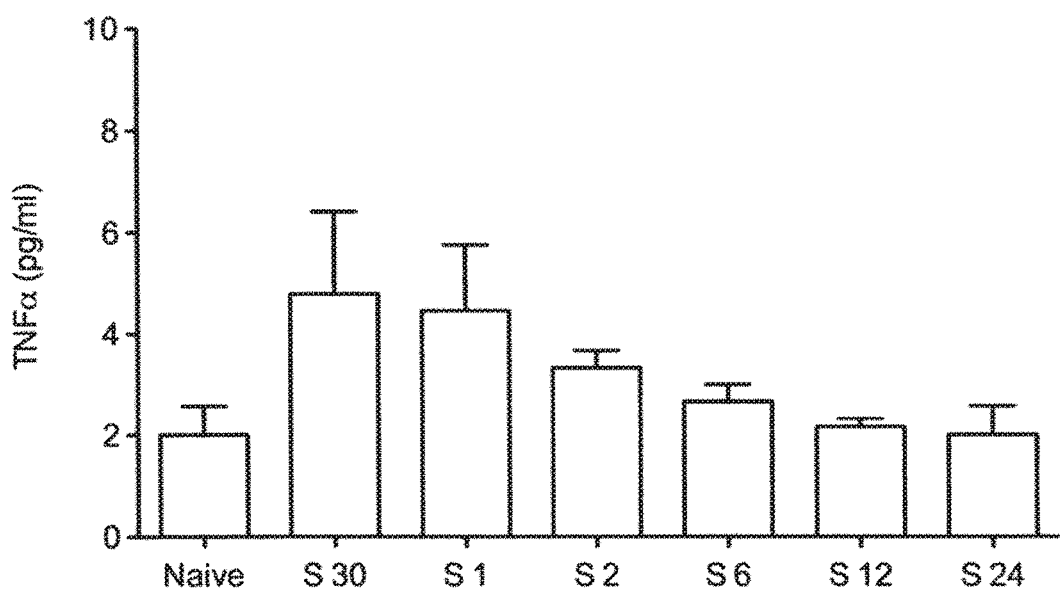
Figure 14:
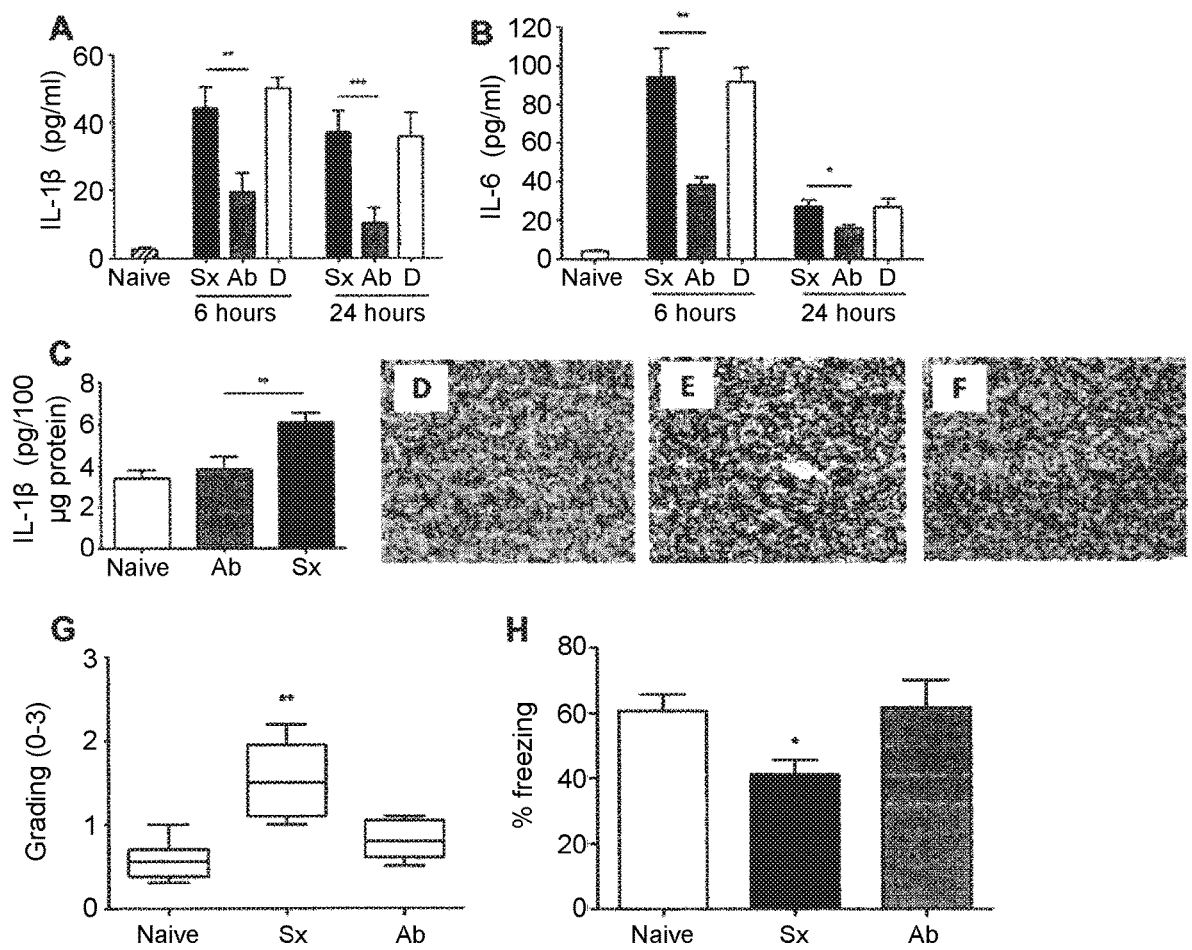
Figure 15:
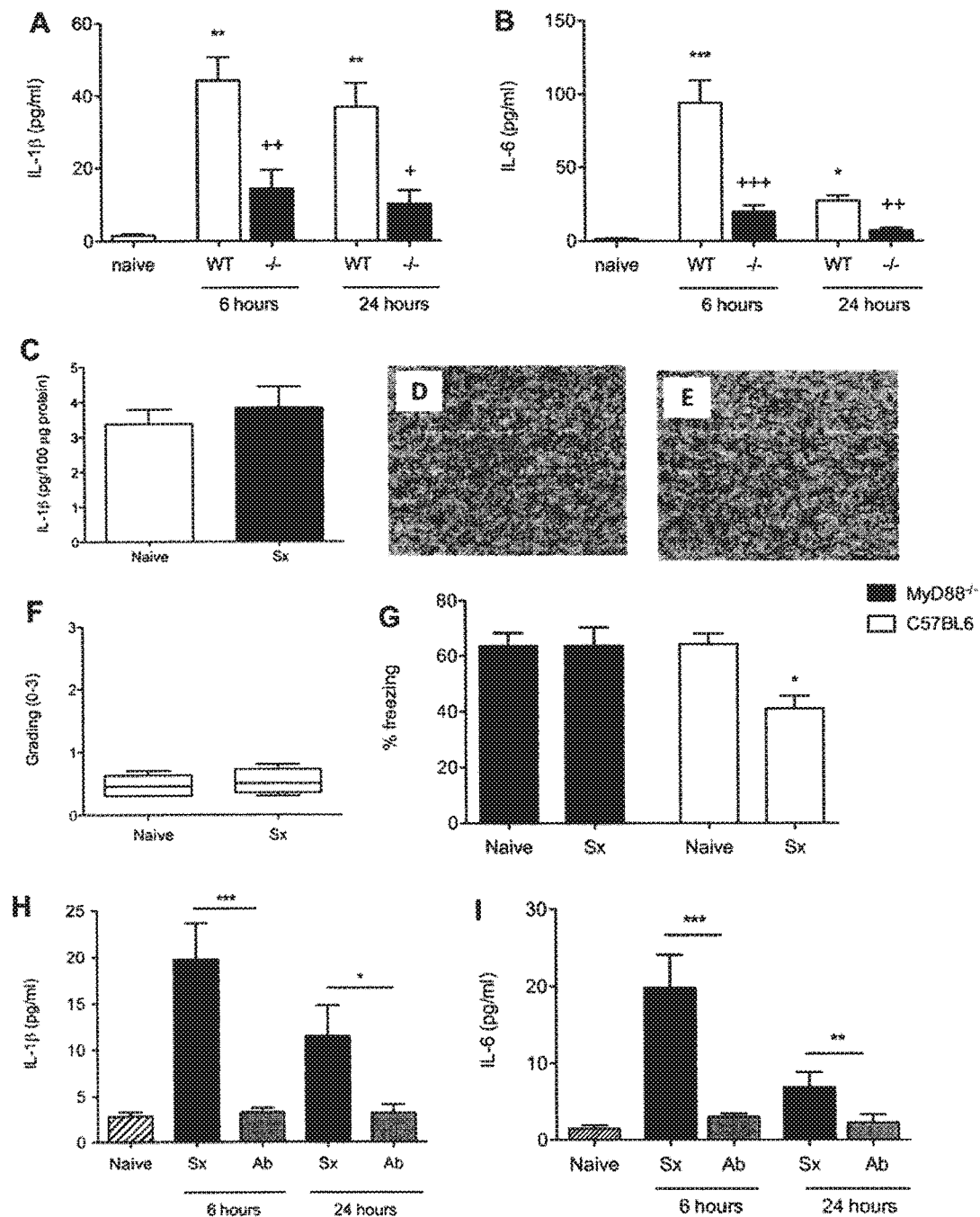
Figure 16:
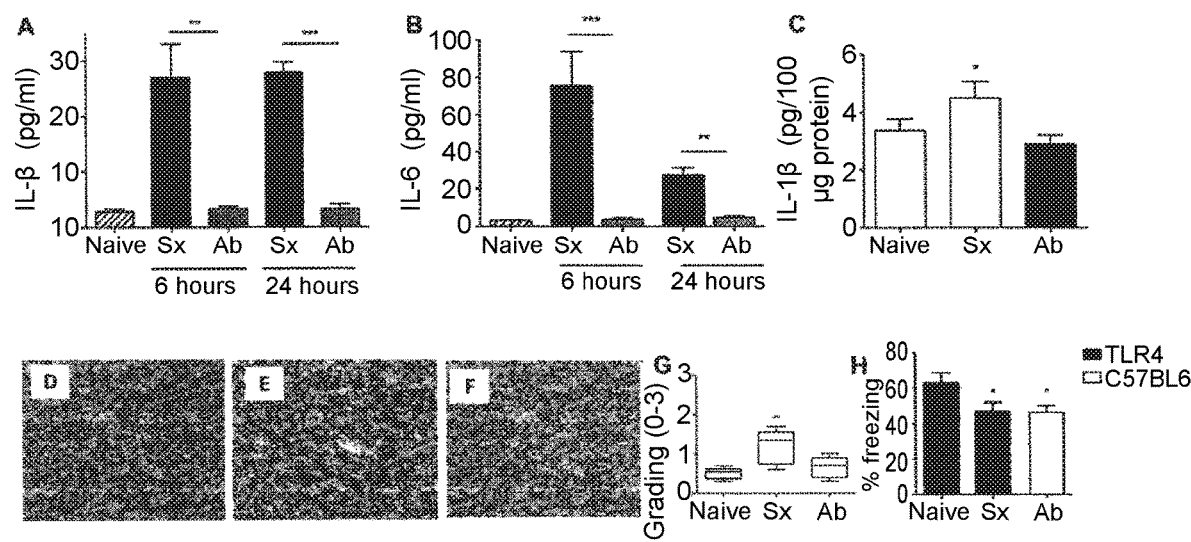
Figure 17:
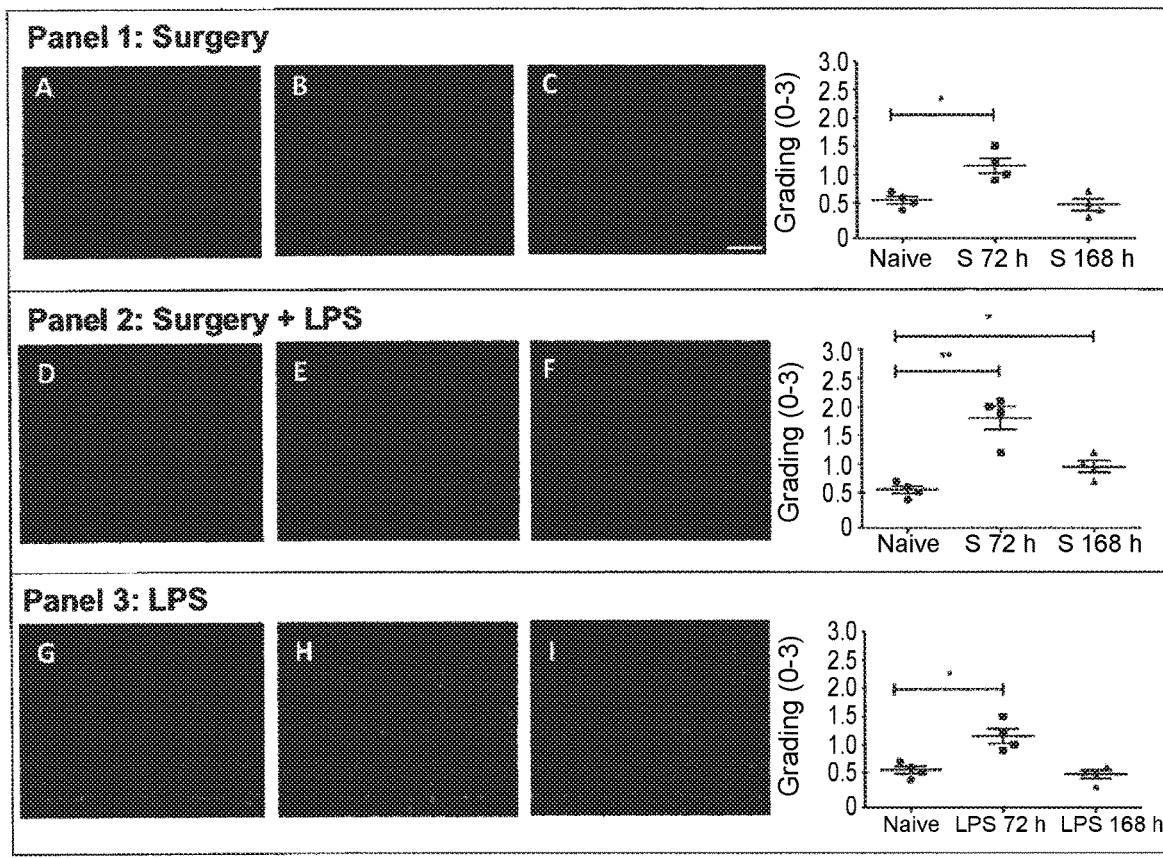
Figure 17:
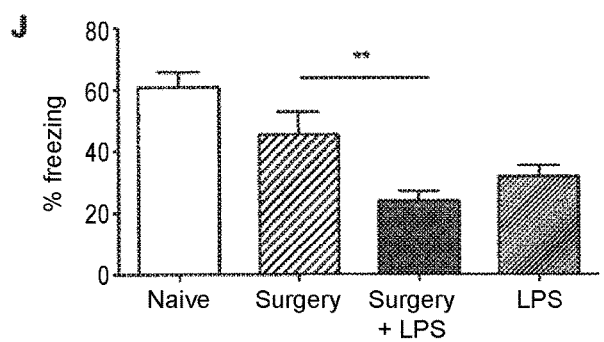
Figure 17:
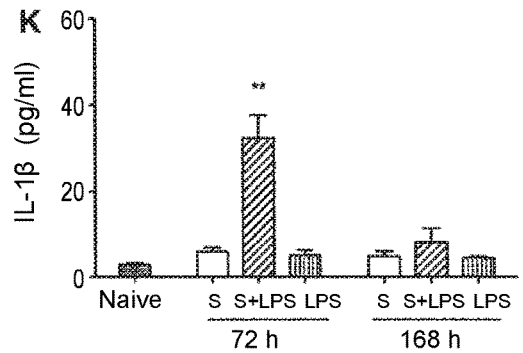

FIG. 13: Systemic TNFα after surgery. Adult mice underwent surgery of the tibia under general anesthesia (Sx). Plasma samples were collected after 30 minutes, 1, 2, 6 and 24 hors following intervention and measured by ELISA. A positive trend was observed within the 1-hour window post surgery. Data are expressed as mean±SEM n=6 and compared by one-way analysis of variance and Student-Newman-Keuls method. S=surgery FIG. 14: Effects of anti-TNFα prophylaxis. Adult mice underwent surgery of the tibia under general anesthesia (Sx), or the same surgical procedure with anti-TNFα prophylaxis 18 hours prior to surgery (Ab). The control group was composed of naïve animals. Preemptive administration of anti-TNFα reduced the amount of systemic IL-1β as measure by ELISA both at 6 hours and 24 hours post intervention (A, p<0.01, *p<0.001 compared to sx respectively). Anti-TNFα prophylaxis also reduced the systemic levels of IL-6 both at 6 and 24 hours following surgery (B, **p<0.01, *p<0.05 compared to sx respectively). Delayed administration of anti-TNFα (legend D) resulted in no changes from surgery assessing both IL-1β and IL-6. Tibia surgery resulted in increased hippocampal levels of IL-1β, which was successfully reduced following treatment (C, p<0.01 vs sx). Immunohistochemistry of microglia in the hippocampus with anti-CD11b one day after surgery. Pictures show CA1 (scale bar 50 μm, 20×) and photomicrographs were blindly scored and microglia activation was graded on a scale 0 (lowest)-3 (highest). Neither naïve (D) or mice treated with anti-TNFα (F) showed evidence of reactive microgliosis. Reactive microglia were found in animals undergoing surgery (E). Median (horizontal bar) with 25th to 75th (box) and 10th to 90th (whiskers) percentiles for immunohistochemical grading (0-3) is presented for data illustration (G). One day after surgery there is an evident reduction in microgliosis following therapy (p<0.01 vs sx). Contextual fear response reveals clear hippocampal-dependent memory impairment (H, * p<0.05 vs naive). Pre-treatment with anti-TNFα ameliorates the memory retention (* p<0.05 vs sx). Data are expressed as mean±SEM n=6 (n=10 for acute behavior) and compared by one-way analysis of variance and Student-Newman-Keuls method. Non parametric data are presented with Kruskal-Wallis followed by Dunn's test. Sx=surgery, Ab=antibody, D=delayed administration of antibody FIG. 15: Roles for both IL-1 and TNFα. Adult MyD88$^{-/-}$ mice underwent surgery of the tibia under general anesthesia (Sx). The control group was composed of MyD88$^{-/-}$ naïve animals. Systemic levels of IL-1β (A, ++p<0.001, +p<0.01 vs surgery WT respectively) and IL-6 (B, +++p<0.001, ++ <0.001 vs surgery WT respectively) were significantly reduced following surgery in MyD88$^{-/-}$ both at 6 and 24 hours. No changes in hippocampal levels of IL-1β were reported (C). Neither naïve (D) nor MyD88$^{-/-}$ undergoing surgery (E) showed evidence of reactive microgliosis. Median (horizontal bar) with 25th to 75th (box) and 10th to 90th (whiskers) percentiles for immunohistochemical grading (0-3) is presented for data illustration (F). Contextual fear response reveals no hippocampal-dependent memory impairment following surgery in MyD88$^{-/-}$ (G). Adult MyD88$^{-/-}$ mice underwent surgery of the tibia under general anesthesia with anti-TNFα prophylaxis 18 hours prior to surgery (Ab). Preemptive administration of anti-TNFα reduced the amount of systemic IL-1β as measure by ELISA to baseline both at 6 hours and 24 hours post intervention (H, \*\*\*p<0.001, \*p<0.01, compared to sx respectively). Levels of IL-6 were also measured, there was a similar reduction with values back to baseline at both time points (H, \*\*\* <0.001, \*\*p<0.01, compared to sx respectively). Data are expressed as mean±SEM n=6 (n=10 for acute behavior) and compared by one-way analysis of variance and Student-Newman-Keuls method. Non parametric data are presented with Kruskal-Wallis followed by Dunn's test. Sx=surgery, Ab=antibody, D=delayed administration of antibody FIG. 16: Anti-TNFα prophylaxis in TLR4$^{-/-}$. Adult TLR4$^{-/-}$ mice underwent surgery of the tibia under general anesthesia (Sx), or the same surgical procedure with anti-TNFα prophylaxis 18 hours prior to surgery (Ab). The control group was composed of TLR4$^{-/-}$ naïve animals. Preemptive administration of anti-TNFα reduced the amount of systemic IL-1β as measure by ELISA to baseline both at 6 hours and 24 hours post intervention (A, \*\*p<0.01, \*\*\*<0.001, compared to sx respectively). There was a similar reduction in levels of IL-6, with values back to baseline at both time points (B, \*\*\*p<0.001, \*\*p<0.01, compared to sx respectively). TLR4$^{-/-}$ showed signs of neuroinflammation but levels of hippocampal IL-1β were reduced by anti-TNFα prophylaxis (C, \*p<0.01 vs sx). Immunohistochemistry of microglia in the hippocampus with anti-CD11b one day after surgery. Pictures show CA1 (scale bar 50 µm, 20×) and photomicrographs were blindly scored and microglia activation was graded on a scale 0 (lowest)-3 (highest). Neither naïve (D) or mice treated with anti-TNFα (F) showed evidence of reactive microgliosis. Reactive microglia were found in TLR4$^{-/-}$ undergoing surgery (E, \*\*p<0.01 vs naïve and ab groups). Median (horizontal bar) with 25th to 75th (box) and 10th to 90th (whiskers) percentiles for immunohistochemical grading (0-3) is presented for data illustration (G). Contextual fear response reveals clear hippocampal-dependent memory impairment similar to WT (H, \* p<0.05 vs naive). Data are expressed as mean±SEM n=6 (n=10 for acute behavior) and compared by one-way analysis of variance and Student-Newman-Keuls method. Non parametric data are presented with Kruskal-Wallis followed by Dunn's test. Sx=surgery, Ab=antibody FIG. 17: Effects of postsurgical LPS on neuroinflammation and behavior. Hippocampi were harvested at days 3 and 7 after surgery and stained with anti-CD1 b. Pictures show CA1 (scale bar 50 µm, 20×) and photomicrographs were blindly scored and microglia activation was graded on a scale 0 (lowest)-3 (highest). PANEL 1: SURGERY. Reactive microglia were found at postoperative day (POD) 3, returning to normal by day 7 (B-C) compared to naïve (A). PANEL 2: SURGERY+LPS. Moderate and mild microgliosis was observed at days 3 and 7, respectively (E-F), compared to control (D). PANEL 3: LPS. Reactive microglia were found at day 3 after LPS injection (H) with no significant changes at day 7 (I), compared to untreated animals (G). Immunohistochemical grading (0-3) illustrates panels 1 and 2. At POD 3 there was a significant difference between surgery and surgery+LPS groups (p<0.05). At POD 7 mild microgliosis was reported following LPS administration (\*p<0.05 vs control) (n=4). Non parametric data are presented with Kruskal-Wallis followed by Dunn's test. Contextual fear response, as measured by freezing behavior, is also impaired in animals receiving surgery followed by LPS exposure compared to naïve and surgery groups (G) (\*\*p<0.05 vs surgery). Data are expressed as mean±SEM (n=10) and compared by one-way analysis of variance and Student-Newman-Keuls method and student t-test for comparison between surgery and surgery with LPS. Mice were injected with LPS (1 mg/kg) 24 h following surgery. Levels of plasma IL-1 were measured by ELISA. At 72 h following surgery, LPS treated animals had a sustained elevation in IL-1β (H; \*\*p<0.01 vs control). No IL-1β was detected after surgery or LPS only at 72 h. Data are expressed as mean±SEM (n=4) and compared by one-way analysis of variance and Student-Newman-Keuls method with Bonferroni corrections.

Example 1: Systemic and Hippocampal IL-1β-Mediated Inflammation Underlie Cognitive Dysfunction Following Surgery While post-operative cognitive dysfunction (POCD) often complicates recovery from major surgery, the pathogenic mechanisms remain unknown. We explored whether systemic inflammation, in response to surgical trauma, triggers hippocampal inflammation and subsequent memory impairment, in a mouse model of orthopedic surgery. Wild type and KO mice (lacking IL-1β receptor, IL-1R$^{-/-}$) underwent surgery of the tibia under general anesthesia. Separate cohorts of animals were tested for memory function with fear conditioning tests, or euthanized at different times to assess levels of systemic and hippocampal cytokines and microglial activation; the effects of interventions, designed to interrupt inflammation (specifically and non-specifically), were also assessed. Surgery caused hippocampal-dependent, memory impairment that was associated with increased plasma cytokines, as well as reactive microgliosis and IL-1β transcription and expression in the hippocampus. Non-specific attenuation of innate immunity with minocycline prevented surgery-induced changes. Functional inhibition of IL-1β, both in IL-1R$^{-/-}$, and in wild type mice pretreated with IL-1 receptor antagonist (IL-1Ra), mitigated the neuroinflammatory effects of surgery and memory dysfunction.

Our results suggest that a peripheral surgery-induced innate immune response triggers an IL-1β-mediated inflammatory process in the hippocampus that underlies memory impairment. This may represent a viable target to interrupt the pathogenesis of post-operative cognitive dysfunction.

Abbreviations

CNS=central nervous system; CS=conditional stimulus; ELISA=enzyme linked immunosorbent assay; IFN=interferon; IL=interleukin; IL-1R$^{-/-}$=Not expressing IL-1 receptor; IL-1Ra=interleukin-1 receptor antagonist; ir=immunoreactive; i.p.=intraperitoneal; i.v.=intravenous; KO=knock out; LPS=lipopolysaccharide; MAC=minimum alveolar concentration; MAPK=mitogen activated protein kinase; MHC=major histocompatibility complex; PKC=protein kinase C; POCD=post-operative cognitive dysfunction; qRT-PCR=quantitative real time polymerase chain reaction; s.c.=subcutaneous; TNF=tumor necrosis factor Material and Methods All the experiments were conducted under Home Office approved license and were performed using 12-14 weeks old male C57-BL6 mice (Harlan, Oxon, UK). IL-1R$^{-/-}$ mice, kindly provided by Professor Nancy Rothwell,[17] were bred in house on a C57BL/6 background and age-matched to wild type counterparts. (For further details please refer to supplemental methods).

Surgery and Pharmacological Treatments.

Mice were subjected to an open tibial fracture of the left hind paw with intramedullary fixation in aseptic conditions under general anaesthesia with isoflurane and analgesia with buprenorphineas previously described[18]. Other groups of animals were not subjected to any intervention (naïve), or received anesthetic/analgesia alone, or underwent surgery with concurrent administration of minocycline, enrofloxacin, or IL-1 receptor antagonist (IL-1Ra). (For further details please refer to supplemental methods).

Real Time PCR (qRT-PCR).

Total RNA was extracted using RNeasy Kit (Qiagen) and quantified. The one-step qRT-PCR was performed on a Rotor-Gene 6000(Corbett Life Science), using Assay-On-Demand premixed Taqmanprobe master mixes (Applied Biosystems). Results are expressed as fold-change. (For further details please refer to supplemental methods).

Cytokine Measurement.

IL-6, TNF-α and IL-1β were measured by ELISA[19] (Biosource, CA; Bender Medsystem, CA, respectively). Hippocampal IL-1β was measured by ELISA (Bender Medsystem, CA), as previously described[20]. To confirm reliability of dilution linearity and spike recovery cytokine measurement were also performed in mice in which inflammation was induced with i.p. LPS (0111:B4, Invivogen, CA). (For further details please refer to supplemental methods).

Immunohistochemistry.

Fixed brains were collected for immunohistochemical DAB staining for CD11b and scored as previously described[21]. (For further details please refer to supplemental methods).

Fear Conditioning Tests.

Mice were conditioned 30 minutes or 3 days prior to intervention by training with two cycles of tone and foot-shock pairings. In delay fear conditioning a foot-shock was administered during the last 2 seconds of each 20 seconds-lasting tone. In trace fear conditioning, the foot-shock onset, lasting 2 seconds as in the previous paradigm, followed a 20-second gap after each tone termination. Three days after conditioning, mice were placed back in the original conditioning chamber for 270 seconds, where no tone or shock were presented, to assess recall of contextual fear memory. After 3 h mice were placed in a novel environment (different context from training) to test for auditory-cued memory. Following an initial baseline period of 135 seconds during which freezing was scored in absence of noise, the auditory cue was presented for the final 135 seconds of the test, and freezing was again recorded. (For further details please refer to supplemental methods).

Data Analysis

Data are expressed as mean±SEM. Statistical analysis was performed with analysis of variance followed by the Student-Newman-Keuls test for numerical data. Student's t test was only used for comparisons between two groups. The non-parametric test of Kruskal-Wallis followed by the Dunn's test was used for categorical data. A p value <0.05 was considered to be of statistical significance.

Results

Surgery Elevates Plasma Concentration of Inflammatory Cytokines IL-1β and IL-6

Plasma IL-1β and IL-6 were unchanged at 2 hours; these peaked at 6 hours (FIG. 1, A-B) increasing by 7-(IL-1β: 42.63 pg/ml, SEM±9.60, n=6, p<0.001) and 20-fold (IL-6: 128.50 pg/ml, SEM±19.64, n=6, p<0.001) above baseline levels, respectively. At 24 h post-surgery, IL-1β and IL-6 were increased 6-(IL-1β: 36.90 pg/ml, SEM±6.54, n=6, p<0.001) and 5-fold (IL-6: 31.74 pg/ml, SEM±5.28, n=6, p<0.05), respectively, compared with naïve animals (IL-1β: 6.09 pg/ml, SEM±1.31, n=6; IL-6: 5.89 pg/ml, SEM±2.10, n=6) (FIG. 1, A-B). TNF-α remained undetectable at all time points under all conditions (data not shown). The administration of anesthetics alone produced no change of cytokines from the baseline levels observed in naïve mice (FIG. 1, A-B). Pre-operative administration of minocycline, an antimicrobial with anti-inflammatory properties[22], reduced the plasma concentrations of cytokines back to pre-surgery levels (FIG. 1, A-B). Conversely enrofloxacin, an antimicrobial with a similar broad-spectrum to that of minocycline but devoid of anti-inflammatory activity, exerted no effect on IL-1β plasma concentration in mice undergoing surgery (FIG. 1, A).

Surgery Increases Hippocampal Cytokines

Hippocampal IL-1β and IL-6 transcription increased 2-fold and 4-fold respectively following surgery at 6 h (FIG. 2, A-B). Consistently, when the expression of hippocampal IL-1β was assessed 6 hours after surgery, there was a 2-fold increase of IL-1β levels (5.53 pg/100 μg of proteins, SEM±0.89, n=7, p<0.05) compared to naïve counterparts (2.73 pg/100 μg of proteins, SEM±0.39, n=7) (FIG. 1, C). IL-1β expression in the hippocampus was not changed in animals exposed to anesthesia alone, from baseline. Minocycline, but not enrofloxacin, reduced IL-1β expression in surgical animals to naïve levels.

Surgery Activates Microglia

LPS-injected mice (positive inflammatory control) exhibited CD11b immunoreactive (ir) microglia in an activated morphologic phenotype characterized by hypertrophy of cell bodies, retraction of processes, an apparent amoeboid morphology, and increased levels of immunoreactivity. Surgery induced similar morphological changes of microglial reactivity at 24 h (FIG. 3) that was significantly different from that of naïve (n=7, p<0.01) and anesthesia-only-treated animals (n=7, p<0.05). Surgery-induced reactive microgliosis was reduced by day 3 (FIG. 3, F) and returned to baseline by 7 days (FIG. 3, G). Administration of minocycline to surgical mice prevented reactive microgliosis (FIG. 3, E-F).

Surgery Impairs Contextual Fear after Delay Conditioning

As expected, there was no difference in freezing time between the groups during training (data not shown). Surgery performed 30 min following training significantly reduced freezing to context that was mitigated by minocycline, but not by enrofloxacin (FIG. 4, A); anesthesia alone produced no change. All the animals displayed the same freezing behavior when exposed to the tone (FIG. 4, B).

Surgery Impairs Memory for Tone in Trace Fear Conditioning

As opposed to delay fear conditioning, trace fear conditioning imposes a brief gap between the tone termination and shock onset. Trace and delay fear conditioning differ in that, in trace, the fear response to both the tone and context highly depends on hippocampal integrity[23]. When exposed to the context, mice undergoing surgery demonstrated a significant reduction of freezing behavior compared with naïve littermates (n=28, p<0.05), consistent with the results from the delay paradigm (FIG. 4, C). Moreover, when the auditory-cued test was carried out, there was a significant difference between surgical and naïve subjects in auditory cued-dependent freezing (n=28, p<0.05), with a reduction in surgical animals (FIG. 4, D).

Surgery does not Induce Inflammation in IL-1R$^{-/-}$ Mice or Mice Treated with IL-1Ra Surgery did not increase circulating IL-1β or hippocampal microgliosis in mice lacking the IL-1 receptor (FIG. 5, A-B-C-D) or in mice pretreated with IL-1Ra. Similarly, surgery did not increase hippocampal microgliosis (FIG. 6, A-B-C) or expression of IL-1β in IL-1Ra treated surgical mice (FIG. 6, D). In the delay fear conditioning paradigm, pre-treatment with IL-1Ra prevented the decrement in post-operative freezing behavior (FIG. 7, A). Results from the auditory-cued test on these groups showed no difference, thereby confirming previous evidence from this study that the amygdala is not functionally impaired by surgery or by IL-1Ra administration (FIG. 7, B).

Contextual Fear Memory is not Impaired in Surgical Animals Undergoing Surgery Three Days after Delay Conditioning The data thus far indicate that hippocampal-dependent retrograde amnesia develops when surgery takes place 30 minutes after training. In order to determine if the memory impairment was caused by interrupted consolidation as opposed to a more permanent loss of hippocampal function, mice underwent surgery 72 hours after delay fear conditioning. The animals were tested for both tone and context memory 3 days later, following the same surgery-to-context time delay as in the previous tests. The test for contextual and acoustic-cued memory showed no statistical difference between surgical and naïve animals (n=28) (FIG. 8, A-B).

Discussion

Data from these studies suggest that inflammation plays a pivotal role in the pathogenesis of POCD as evidenced by the protection afforded surgical animals by minocycline, a non-specific inhibitor of inflammation. Also, we demonstrated that IL-1β is likely to have a causal role in conveying the inflammatory signal from a peripheral surgical site to the brain. Hippocampal inflammation follows peripheral surgery as demonstrated by a local increase in the transcription and expression of IL-1β as well as reactive microgliosis. We show that attenuation of the IL-1β response to surgery prevents post-operative memory dysfunction. Post-surgical impairments for contextual fear memory and for auditory-cued memory in trace, but not for auditory-cued memory in delay conditioning, also suggest that postoperative memory dysfunction is derived from the hippocampus rather than other components of the fear circuit, such as auditory thalamic, amygdalar or periaqueductal gray regions.

The impaired hippocampal-dependent contextual fear memory after aseptic surgery is similar to the impairment in contextual fear conditioning that follows intraperitoneal administration of LPS in a model of peripheral inflammation caused by infection[24]. Also, neither LPS[24] nor surgery disrupts delay auditory-cued memories. That the hippocampus is critical for post-surgery cognitive impairment is confirmed by the trace conditioning procedure in which impaired freezing responses were observed to both context and tone.

A possible causality relationship between surgery, inflammation and memory impairment was suggested by the effects of minocycline administration in reducing surgery-induced peripheral and hippocampal cytokine expression, reactive microgliosis and behavioral impairment; minocycline also restored behavioral impairment in a mouse model of LPS-induced inflammation[25]. Minocycline reduces microglial activation through the inhibition of interferon (IFN)-γ-induced PKCα/βII phosphorylation and both PKCα/βII and IRF-1 nuclear translocation, ultimately converging in the partial down regulation of MHC II proteins[26]. Importantly, minocycline inhibits the transcription factor p38-MAPK, which plays a pivotal role in the cascade leading to the biosynthesis of cytokines such as IL-1 and IL-6 as well as other pro-inflammatory mediators[27]. Moreover, at a functional level, minocycline appears to improve behavioral performance in a mouse model of spatial learning and memory through reduction of microglial activation[28].

Despite the aseptic technique employed, it is possible to ascribe the advent of post-operative hippocampal inflammation and cognitive dysfunction and its attenuation by an antimicrobial (minocycline) to an infective process following surgical intervention. However, in this study no clinical evidence of infection was seen in any of the animals as shown in previous studies[18]. Importantly, in our study, the administration of enrofloxacin, a wide spectrum antibiotic often used in rodents but devoid of any anti-inflammatory properties, did not improve any of the surgery-induced effects.

It could be argued that pain may be a confounding factor producing immobility and thus influencing the extent of "freezing" in the behavioral tests. However, our model of surgery aimed to reproduce routine clinical settings and, accordingly, administration of an analgesic opiate (buprenorphine) in our experiments likely mitigated surgical pain. If nociceptive input caused the animals to restrict movement of their affected limb during retrieval of context or auditory-cued memories, we would have expected to see more, and not less, freezing. It is of some importance to note that even pain produced by subcutaneous injection of formalin into a hind paw does not disrupt freezing seen with contextual fear conditioning[29]. Moreover, a possible interference from pain in the extinction tests was addressed by the testing for memory impairment in the setting in which surgery was delayed by three days after conditioning. Since the delay between surgery and retrieval tests in this experiment was the same as in the other implemented fear conditioning experiments, it is reasonable to conclude, based on results showing no differences between surgical and naïve animals in memory retrieval, that there was no interference from post-operative pain in all the fear conditioning retrieval tests employed in this study.

In the activated state, microglia are capable of mounting macrophage-type innate immunity and secrete pro-inflammatory cytokines, reactive oxygen species, excitotoxins (such as glutamate) and neurotoxins such as β-amyloid precursor protein[30]. Activation of microglia has been linked to the cognitive dysfunction that is seen in sickness behavior and is causally related to impairment of long-term potentiation in advanced age[31]. Thus, increased microglial reactivity, and the associated inflammatory processes, are capable of producing the molecular changes that attenuate signalling pathways involved in memory formation[32].

We have demonstrated that IL-1β plays a pivotal role in surgery-induced cognitive dysfunction[24,33]. Peripheral cytokines can signal to the brain via both blood and neural routes thereby stimulating cytokine production by glial cells[34,35,36], especially in the hippocampus[37,20]. Evidence of increased hippocampal transcription of IL-1β suggests the possible role of microglia in the de novo production of cytokines in our mouse model. The specificity of IL-1β involvement is emphasized by the experiments involving IL-1R$^{-/-}$ mice and wild type mice treated with IL-1Ra in which microglial activation in the hippocampus is no longer triggered after surgery. IL-1β interferes with hippocampal long-term potentiation[19,38] that has been viewed as an essential electrophysiological correlate of memory[39]. IL-1β acts either directly, or indirectly through microglial activation, on the intracellular neuronal mechanisms that stabilize the long-term plasticity necessary for memory such as protein synthesis. Loss of memory induced by IL-1β is unlikely to be caused by permanent damage, retrieval failure or an inability to perform the freezing response, as such deficits would have also appeared when surgery occurred three days after training.

We have shown that elevated systemic and brain tissue cytokines, as well as hippocampal microglial activation, are all reduced by treatment with peripherally injected minocycline or IL-1Ra. While these data suggest that humoral, rather than, or in addition to, neural factors are involved[42], further studies are required. Attenuation of the neuroinflammatory process with either minocycline or by interference with IL-1β signalling prevents the post-surgical cognitive dysfunction. This neuroinflammatory process and its initiation, represents a realistic target for therapeutic interventions with major potential benefits for the ageing surgical population. Subsequent studies to elucidate whether the neuroinflammatory response can be modulated by anesthetic agents or by selective anti-inflammatory strategies may be helpful in ameliorating the adverse consequences of post-operative cognitive decline.

Supplementary Material

Animals and Surgical Methods

All the experiments were conducted under Home Office approved license and were performed using 12-14 weeks old male C57-BL6 mice (Harlan, Oxon, UK) housed in groups of up to 4 animals/cage, under a 14:10 hours light-dark cycle, in a constant temperature and humidity controlled environment, with free access to food and water. Acclimation to light/dark cycle for a minimum of 7 days preceded any intervention or assessment. All the animals were checked on a daily basis for signs of infection. Evidence of poor grooming, huddling, piloerection, weight loss, wound dehiscence, muscle twitching, back arching and abnormal activity, were recorded.

IL-1R$^{-/-}$, kindly provided by Professor Nancy Rothwell, University of Manchester, were generated as previously described[1], were bred in house on a C57BL/6 background and age-matched to wild type counterparts.

Mice were randomly assigned to the following groups: surgery under general anesthesia (S), surgery under general anesthesia plus minocycline (M), surgery under general anesthesia plus enrofloxacin (E), surgery under general anesthesia plus interleukin-1 receptor antagonist (IL-1Ra) (I), surgery in IL1R$^{-/-}$ mice under general anesthesia (K), general anesthesia without surgery (A), and no intervention (naïve wild-type, or naïve IL1R$^{-/-}$). Under aseptic conditions, groups of mice were subjected to an open tibial fracture of the left hind paw with an intramedullary fixation as previously described[2]. Briefly, isoflurane (Abbot Laboratories Ltd., Queensborough, Kent, UK) 2.1% in air (1.5 MAC)[3] and buprenorphine (Reckitt Benckiser Healthcare Ltd, Hull, UK) 0.1 mg/kg subcutaneously (sc), were given to provide both surgical anesthesia and extended post-operative analgesia for the surgical intervention and post-surgical recovery. After shaving the overlying skin and disinfecting with chlorhexidine gluconate 0.5% and isopropyl alcohol 70% (PDI, Orangeburg, N.Y., USA) a fracture of the tibial shaft was created under direct vision. A longitudinal incision was made through the skin and fascia lateral to the tibia to expose the bone. A 0.5 mm hole was drilled just above the proximal third of the tibia to insert an intramedullary 0.38 mm diameter stainless steel fixation wire. Subsequently, the fibula and the muscles surrounding the tibia were isolated, the periosteum stripped over a distance of 10 mm circumferentially and an osteotomy was performed with scissors at the junction of the middle and distal third of the tibia. The skin was sutured with 8/0 Prolene and intra-operative fluid loss was replaced with 0.5 ml of subcutaneously injected normal saline. Mice in groups M, E and I also received an intraperitoneal (i.p.) injection of minocycline (Sigma, Poole, UK) 40 mg/kg 2 hours prior to surgery and once daily until assessment of outcome, or enrofloxacin 10 mg/kg 2 hours prior to surgery and twice daily thereafter until assessment of outcome or IL-1Ra 100 mg/kg prior to surgery, respectively. Mice in group A received anesthesia (isoflurane 1.5 MAC for 20 minutes) and analgesia (buprenorphine 0.1 mg/kg) with no surgical intervention or other treatment. All the animals were injected twice daily with experimental drugs or equivalent volumes (0.1 ml) of saline. Mice were allowed free, unrestricted food and water intake following recovery from the procedure. Mice from each treatment group were randomly assigned to two different assessment groups for either harvesting blood and tissue samples or for cognitive behavior, in order to obviate possible confounding effects of fear conditioning testing[4] on inflammatory markers.

Conditioning Chamber and Fear Conditioning

Fear conditioning is used to assess learning and memory in rodents, which are trained to associate a conditional stimulus (CS), such as a tone, with an aversive, unconditional stimulus (US), such as a foot-shock[5]. Freezing behavior is an indicator of aversive memory that is measured when subjects are re-exposed to the CS. The environment, or context, in which the animals are trained, represents a more sophisticated example of CS. In delay fear conditioning, where the tone and shock are temporally contiguous, lesions of the amygdala disrupt recall of fear responses to both auditory cue and context, whereas lesions of the hippocampus disrupt context-related but not auditory cue-related memories[5,6].

The behavioral study was conducted using a conditioning chamber (Med. Associates Inc., St. Albans, Vt., USA). The back- and the side-walls of the chamber were made of aluminium, whereas the front door and the ceiling were of transparent Plexiglas. The floor of the chamber consisted of 36 stainless steel rods (1 mm diameter) spaced 0.5 cm apart (center-to-center). The rods were wired to a shock generator and scrambler for the delivery of foot shock. Prior to testing, the chambers were cleaned with a 5% sodium hydroxide solution. Background noise (60 dB, A scale) was provided by means of a fan positioned on one of the sidewalls. An infrared video camera, mounted in front of the chamber captured behavior (Video Freeze, Med. Associates Inc., St. Albans, Vt., USA). In order to make the environment (context) different for acoustic-cued behavioural assessment, the shape of the chamber was changed from rectangular to triangular, the ceiling colour was black instead of white, the flooring rods were covered with a smooth surface and background noise was removed. Assessment of the acoustic-cued behavior of tone-to-shock pairings in the novel context tests amygdalar, rather than hippocampal function[7]. Video data were collected by an infrared camera positioned in front of the chamber and was stored in a computer compatible format (Video Freeze, Med. Associates Inc., St. Albans, Vt., USA). On each day of testing, mice were transported to the behavioral room and left undisturbed for at least 20 minutes before placing them into the conditioning chamber. Freezing was recognized by the software as a total lack of movement excluding breathing but including movement of fur, vibrissae and skeleton. The percentage of time spent freezing over the total time spent in the chamber to accomplish the test was used to score memory and learning abilities. A decrease in the percentage of time spent freezing indicated impairment of these abilities.

In delay fear conditioning, training consisted of placing the mouse in the conditioning chamber and allowing exploration of the context for 100 seconds. Next, an auditory cue (75-80 dB, 5 kHz), the conditional stimulus (CS), was presented for 20 seconds. A 2-second foot-shock (0.75 mAmp), the unconditional stimulus (US), was administered during the final 2 seconds of the CS. This procedure was repeated with an inter-trial interval of 100 seconds, and the mice were removed from the chamber 30 seconds later. Trace fear conditioning differed from delay in that the 2-second foot-shock was administered 20 seconds after termination of the tone. With the termination of the trial, which lasted a total of 270 seconds, every mouse was taken individually to the surgery room, within 30 minutes. All the animals, regardless to the specific intervention, underwent the same handling, including naïve animals. After testing, animals were returned to their housing cage. Three days after conditioning, mice were transported again to the behavioral room and left undisturbed for 15 minutes. They were returned into the same chamber where training had occurred for a context test lasting 270 seconds, during which no tones or foot-shocks were delivered. Freezing behavior in response to context was recorded by the software. At the end of the test, mice were individually returned to their home cage. Approximately 3 hours later, freezing was recorded in a novel environment and in response to the auditory cue. The novel environment resulted from modifications to the basic chamber consisting of an opaque Plexiglas triangle; a Plexiglas floor; increased illumination; no background noise from the fan; and a different smell. Mice were placed in this novel environment, and time sampling was used as baseline during which freezing was scored for 135 seconds. The auditory cue was then presented for 135 seconds, and freezing was again recorded.

Quantification of IL-1β Transcripts by Quantitative Real Time PCR (qRT-PCR).

The hippocampus was rapidly extracted under a dissecting microscope, placed in RNA-later solution (Applied Biosystems, Ambion) and stored at 4° C. Total RNA was extracted using RNeasy Kit (Qiagen) and quantified. The one-step qRT-PCR was performed on a Rotor-Gene 6000 (Corbett Life Science), using Assay-On-Demand premixed Taqman probe master mixes (Applied Biosystems). Each RNA sample was run in triplicate, and relative gene expression was calculated using the comparative threshold cycle ΔΔCt and normalized to beta-actin (ACTB). Results are expressed as fold-change.

Cytokine Measurement

Blood was collected by cardiac puncture into heparin coated syringes whilst animals were under terminal anesthesia with pentobarbital. Samples were centrifuged at 3500 rpm for 10 minutes at 4° C. and plasma was collected and stored frozen at −80° C. until assaying. IL-6 and TNF-α were measured in plasma using a commercially available ELISA kit (Biosource, CA), whereas the ELISA kit for IL-1β was from a different manufacturer (Bender Medsystem, CA). The sensitivies of the assays were 1.2 pg/ml for IL-1β, 3 pg/ml for TNF-α and 3 pg/ml for IL-6. Positive controls consisted of animals treated with i.p. LPS (0111:B4, Invivogen, CA) (data not shown).

Under terminal anesthesia with pentobarbital, each mouse was euthanized and the brain quickly removed following decapitation. The hippocampus was dissected under microscopy on a frosted glass plate placed on top of crushed ice, then snap frozen and stored at −80° C. until processing. Each hippocampus was added to Iscove's culture medium containing 5% fetal calf serum (FCS) and a cocktail of enzyme inhibitors (in mM: 100 amino-n-caproic acid, 10 EDTA, 5 benzamidine-HCl, and 0.2 phenylmethylsulfonyl fluoride). The proteins were mechanically dissociated from tissue by means of sonication in a container plunged in ice. This consisted of 3 cycles of cell disruption each lasting 3 seconds. Sonicated samples were centrifuged at 10000 rpm for 10 minutes at 4° C. Supernatants were collected and stored at −80° C. until the ELISA was carried out. IL-1 was measured in the supernatant from hippocampal extracts, which were appropriately diluted prior to measurement to fall on the linear portion of the sigmoid curve, using a commercially available ELISA kit (Bender Medsystem, CA). The sensitivity of the assay was 1.2 pg/ml. The ELISA kit was validated for use with brain tissues. Samples collected from mice treated with LPS (0111:B4, Invivogen, CA) 3 mg/kg i.p. were used to confirm reliability of dilution linearity and spike recovery (data not shown).

Immunohistochemistry

Under terminal anesthesia with pentobarbital, mice were euthanized and perfused transcardially with ice-cold heparinized 0.1M phosphate buffer solution (PBS) followed by 4% paraformaldehyde in 0.1M PBS at pH 7.4 (VWR International, Lutterworth, Leicester, UK). The brains were harvested and post-fixed in 4% paraformaldehyde in 0.1M PBS at 4° C. and cryoprotected in 0.1M PBS solutions containing 15% sucrose for 24 hours (VWR International, Lutterworth, Leicester, UK) and then 30% sucrose for a further 48 hours.

Brain tissue was freeze-mounted in OCT embedding medium (VWR International, Lutterworth, Leicester, UK). 30 μm thick coronal sections of the hippocampus were cut sequentially in groups of 6 and mounted on Superfrost® plus slides (Menzel-Glaser, Braunschweig, Germany).

The rat anti-mouse monoclonal antibody, anti-CD11b (low endotoxin, clone M1/70.15) in the concentration of 1:200 (Serotec, Oxford, UK) was used to label microglia. Visualization of immunoreactivity for CD11b was achieved using the avidin-biotin technique (Vector Labs, Cambridge, UK) and a goat anti-rat secondary antibody (Chemicon International, CA, USA) at a concentration of 1:200. A negative control omitting the primary antibody was performed in all experiments. A positive control group consisted of animals injected i.p. with LPS 3 mg/kg[8]. Immunohistochemical photomicrographs were obtained with an Olympus BX-60 microscope and captured with a Zeiss KS-300 colour 3CCD camera. The assessment of staining, by an observer that was blinded to the interventional group, was based upon a 4-point categorical scale modified from Colburn and colleagues[9], which uses a combined evaluation of the level of microglial activation from both cell morphology and immunoreactivity.

REFERENCES

1. Forton D M, Allsop J M, Main J, Foster G. R, Thomas H C, Taylor-Robinson S D Evidence for a cerebral effect of the hepatitis C virus. Lancet 2001; 358: 38-9.
2. Hopkins R O, Weaver L K, Collingridge, D, et al. Two-year cognitive, emotional, and quality-of-life outcomes in acute respiratory distress syndrome. Am J Respir Crit Care Med 2005; 171: 340-7.
3. Heflin L H, Meyerowitz B E, Hall P, Lichtenstein P, Johansson B, Pedersen N L, et al. Cancer as a risk factor for long-term cognitive deficits and dementia. J Natl Cancer Inst 2005; 97: 854-6.
4. Capuron L, Lamarque D, Dantzer R, Goodall G. Attentional and mnemonic deficits associated with infectious disease in humans. Psychol Med 1999; 29: 291-7.
5. Dantzer R. Cytokine-induced sickness behaviour: a neuroimmune response to activation of innate immunity. Eur J Pharmacol 2004; 500: 399-411.
6. Bolles R C & Fanselow M S. A perceptual-defensive-recuperative model of fear and pain. Behavioral & Brain Sciences 1980; 3: 291-301.

7. Moller J T, Cluitmans P, Rasmussen L S, Hounx P, Rasmussen H, Canet J, et al. Long-term postoperative dysfunction in the elderly. ISPOCD 1 Study Lancet 1998; 351: 857-61.
8. Bohnen N, Warner M A, Kokmen E, Kurland L T. Early and midlife exposure to anesthesia and age of onset of Alzheimer's disease. Int J Neurosci 1994; 77: 181-5.
9. Monk T G, Weldon B C, Garvan C W, Dede D E, van der Aa M T, Heilman K M, et al. Predictors of cognitive dysfunction after major noncardiac surgery. Anesthesiology 2008; 108: 18-30.
10. Johnson T, Monk T, Rasmussen L. S, Abildstrom H, Houx P, Korttila K, et al. Postoperative cognitive dysfunction in middle-aged patients. Anesthesiology 2002; 96: 1351-7.
11. Newman S, Stygall J, Hirani S, Shaefi S, Maze, M. Postoperative cognitive dysfunction after noncardiac surgery: a systematic review. Anesthesiology 2007; 106: 572-90.
12. Culley D J, Baxter M, Yukhananov R, Crosby G. The memory effects of general anesthesia persist for weeks in young and aged rats. Anesth Analg 2003; 96: 1004-9.
13. Campbell D N, Lim M, Muir M K, O'Sullivan G, Falcon M, Fison P, et al. prospective randomised study of local versus general anaesthesia for cataract surgery. Anaesthesia 1993; 48: 422-8.
14. Williams-Russo P, Sharrock N E, Mattis S, Szatrowski T P, Charlson M E. Cognitive effects after epidural vs general anesthesia in older adults. A randomized trial. JAMA 1995; 274: 44-50.
15. Dinarello C A. Biologic basis for interleukin-1 in disease. Blood 1996; 87: 2095-147.
16. Goshen I, Kreisel T, Ounallah-Saad H, Renbaum P, Zalzstein Y, Ben-Hur T, Levy-Lahad E, Yirmiya R. A dual role for interleukin-1 in hippocampal-dependent memory processes. Psychoneuroendocrinology 2007; 32: 1106-15.
17. Labow M, Shuster D, Zetterstrom M, Nunes P, Terry R, Cullinan E B, et al. Absence of IL-1 signaling and reduced inflammatory response in IL-1 type I receptor-deficient mice. J Immunol 1997; 159: 2452-61.
18. Harry L E, Sandison A, Paleolog E M, Hansen U, Pearse M F, Nanchahal J. Comparison of the healing of open tibial fractures covered with either muscle or fasciocutaneous tissue in a murine model. J Orth Res 2008; 26: 1238-44.
19. Cunningham A J, Murray C A, O'Neil L A J, Lynch M A, O'Connor J J. Interleukin-1 (IL-1) and tumor necrosis factor (TNF) inhibit long-term potentiation in the rat dentate gyrus in vitro. Neurosci Lett 1996; 203: 17-20.
20. Nguyen K T, Deak T, Owens S M, Kohno T, Fleshner M, Watkins L R, Maier S. F. Exposure to acute stress induces brain IL-1β protein in the rat. J Neurosci 1998; 18: 2239-46.
21. Colburn R W, DeLeo J A, Rickman A J, Yeager M P, Kwon P, Hickey W F. Dissociation of microglial activation and neuropathic pain behaviors following peripheral nerve injury in the rat. J Neuroimmunol 1997; 79: 163-75.
22. Amin A R, Attur M G, Thakker G D, Patel P D, Vyas P R, Patel R N et al. A novel mechanism of action of tetracyclines: effects on nitric oxide synthases. Proc Natl Acad Sci USA. 1996; 93: 14014-19.
23. Chowdhury N, Quinn J J, Fanselow M S. Dorsal hippocampus involvement in trace fear conditioning with long, but not short, trace intervals in mice. Behav Neuroscience 2005; 119: 1396-1402.
24. Pugh C R, Kumagawa K, Fleshner M, Watkins L R, Maier S F, Rudy J W. Selective effects of peripheral lipopolysaccharide administration on contextual and auditory-cue fear conditioning. Brain Behav Immun 1998; 12: 212-29.
25. Henry C J, Huang Y, Wynne A, Hanke M, Himler J, Bailey M T, et al. Minocycline attenuates lipopolysaccharide (LPS)-induced neuroinflammation, sickness behaviour, and anhedonia. J Neuroinflamm 2008; 5: 15-29.
26. Nikodemova M, Watters J J, Jackson S J, Yang S K, Duncan I D. Minocycline down-regulates MHC II expression in microglia and macrophages through inhibition of IRF-1 and protein kinase C (PKC)alpha/betaII. J Biol Chem 2007; 282: 15208-16.
27. Du Y, Ma Z, Lin S, Dodel R C, Gao F, Bales K R, et al. Minocycline prevents nigrostriatal dopaminergic neurodegeneration in the MPTP model of Parkinson's disease. Proc Natl Acad Sci USA 2001; 98: 14669-74.
28. Fan R, Xu F, Previti M L, Davis J, Grande A M, Robinson J K, et al. Minocycline reduces microglial activation and improves behavioral deficits in a transgenic model of cerebral microvascular amyloid. J Neurosci 2007; 27: 3057-63.
29. Fanselow M S & Baackes M P. Conditioned fear-induced opiate analgesia on the formalin test: Evidence for two aversive motivational systems. Learning & Motivation, 1982; 13: 200-21.
30. van Rossum D & Hanisch U K. Microglia. Metab Brain Dis 2004; 19: 393-411.
31. Griffin R, Nally R, Nolan Y, McCartney Y, Linden J, Lynch M A The age-related attenuation in long-term potentiation is associated with microglial activation. J Neurochem 2006; 99: 1263-72.
32. Maher F O, Clarke R M, Kelly A, Lynch M A. Interaction between interferon gamma and insulin-like growth factor-1 in hippocampus impacts on the ability of rats to sustain long-term potentiation. Journal of Neurochemistry 2006; 96: 1560-71.
33. Barrientos R M, Higgins E A, Sprunger D B, Watkins L R, Rudy J W, Maier S F. Memory for context is impaired by a post context exposure injection of interleukin-1 beta into dorsal hippocampus. Behav Brain Res 2002; 134: 291-8.
34. Godbout J P, Chen J, Abraham J, Richwine A F, Berg B M, Kelley K W, et al. Exaggerated neuroinflammation and Sickness Behaviour in aged mice following activation of the peripheral innate immune system. FASEB Journal 2005; 19: 1329-31.
35. Eriksson C, Nobel S, Winblad B, Schultzberg M. Expression of interleukin 1 alpha and beta, and interleukin 1 receptor antagonist mRNA in the rat central nervous system after peripheral administration of lipopolysaccharides. Cytokine 2000; 12: 423-31.
36. Maier S F, Goehler L E, Fleshner M, Watkins L R. The role of the vagus nerve in cytokine-to-brain communication. Ann New York Acad Sci 1998; 840: 289-300.
37. Ban E, Haour F, Lenstra R. Brain interleukin 1 gene expression induced by peripheral lipopolysaccharide administration. Cytokine 1992; 4: 48-54.
38. Vereker E, Campbell V, Roche E, McEntee E, Lynch M A. Lipopolysaccharide inhibits long term potentiation in the rat dentate gyrus by activating caspase-1. J Biol Chem 2000; 275: 26252-8.
39. Morris R G. Synaptic plasticity and learning: selective impairment of learning rats and blockade of long-term potentiation in vivo by the N-methyl-D-aspartate receptor antagonist AP5. J Neurosci 1989; 9: 3040-57.
40. Wan Y, Xu J, Ma D, Zeng Y, Cibelli M, Maze M. Postoperative impairment of cognitive function in rats: a possible role for cytokine-mediated inflammation in the hippocampus. Anesthesiology 2007; 106: 436-43.
41. Rosczyk H A, Sparkman N L, Johnson R W. Neuroinflammation and cognitive function in aged mice following minor surgery. Exp Gerontol 2008; 43: 840-6.
42. Wieczorek M, Swiergiel A H, Pournajafi-Nazarloo H, Dunn A J. Physiological and behavioral responses to interleukin-1beta and LPS in vagotomized mice. Physiol Behav 2005; 85: 500-11.

REFERENCES FOR SUPPLEMENTAL METHODS

1. Labow M, Shuster D, Zetterstrom M, Nunes P, Terry R, Cullinan E B, et al. Absence of IL-1 signaling and reduced inflammatory response in IL-1 type I receptor-deficient mice. J Immunol 1997; 159: 2452-61.
2. Harry L E, Sandison A, Paleolog E M, Hansen U, Pearse M F, Nanchahal J. Comparison of the healing of open tibial fractures covered with either muscle or fasciocutaneous tissue in a murine model. J Orth Res 2008; 26: 1238-44.
3. Engelhardt T, Lowe P R, Galley H F, Webster N R Inhibition of neuronal nitric oxide synthase reduces isoflurane MAC and motor activity even in nNOS knockout mice. Br J of Anesth 2006; 3: 361-6.
4. Nguyen K T, Deak T, Owens S M, Kohno T, Fleshner M, Watkins L R, Maier S. F. Exposure to acute stress induces brain IL-1b protein in the rat. J Neurosci 1998; 18: 2239-46.
5. Kim J J & Fanselow M S. Modality-specific retrograde amnesia of fear. Science. 1992; 256: 675-7.
6. Phillips R G & LeDoux J E Differential contribution of amygdala and hippocampus to cued and contextual fear conditioning. Behav Neurosci. 1992; 106: 274-85.
7. Quinn J J, Oommen S S, Morrison G E, Fanselow M S. Post-training excitotoxic lesions of the dorsal hippocampus attenuate forward trace, backward trace, and delay fear conditioning in a temporally specific manner. Hippocampus 2002; 12: 495-504.
8. Qin L, Wu X, Block M L, Liu Y, Breese G R, Hong J S, et al. Systemic LPS causes chronic neuroinflammation and progressive neurodegeneration. Glia 2007; 55: 453-62.
9. Colburn R W, DeLeo J A, Rickman A J, Yeager M P, Kwon P, Hickey W F. Dissociation of microglial activation and neuropathic pain behaviors following peripheral nerve injury in the rat. J Neuroimmunol 1997; 79: 163-75.

Example 2: Cytokines Inform Sepsis-Induced Cognitive Dysfunction

The impact of pro-inflammatory cytokines on neuroinflammation and cognitive function after lipopolysaccharide (LPS) challenge remains elusive. Herein we provide evidence that despite a temporal correlation between high-mobility group box 1 (HMGB-1), microglia activation, and cognitive dysfunction, targeting of the interleukin (IL)-1 pathway is sufficient to reduced inflammation and ameliorate the disability.

Endotoxemia was induced in wild-type and IL-1R$^{-/-}$ mice by intra peritoneal injection of *E. Coli* LPS (1 mg/kg). Markers of inflammation were assessed both peripherally and centrally, and correlated to behavioral outcome using trace fear conditioning.

Plasma increase in tumor necrosis factor-α (TNFα) peaked at 30 minutes after LPS challenge. Up-regulation of IL-1β, IL-6 and HMGB-1 was more persistent, with detectable levels up to day 3. A 15-fold increase in IL-6 and a 6.5-fold increase in IL-1β mRNA at 6 hours post intervention ($p<0.001$ respectively) was found in the hippocampus. Reactive microgliosis was observed both at days 1 and 3, and was associated with elevated HMGB-1 and impaired memory retention ($p<0.005$). Preemptive administration of IL-1 receptor antagonist (IL-1Ra) significantly reduced plasma cytokines and hippocampal microgliosis and ameliorated cognitive dysfunction without affecting HMGB-1 levels. Similar results were observed in LPS-challenged mice lacking the IL-1 receptor to the wild type mice treated with IL-1 Ra.

These data suggest that by blocking IL-1 signaling, the inflammatory cascade to LPS is attenuated, thereby reducing microglial activation and preventing the behavioral abnormality. This amelioration appears to be independent of HMGB-1 up regulation.

Material and Methods

Animals.

All the experiments were conducted under the UK Home Office approved license. Wild type C57BL/6 male mice, 12-14 weeks old, weighting 25-30 g were used and housed in groups of five in a 12-h-12-h light dark cycle, with controlled temperature and humidity with free access to food and water. IL-1R$^{-/-}$ (kindly provided by Nancy Rothwell, University of Manchester [13]) were bred in-house on a C57BL/6 background and age-matched to wild type counterparts. Seven days of acclimatization were allowed before starting any experiment. All the animals were checked on a daily basis and evidence of poor grooming, huddling, piloerection, weight loss, back arching and abnormal activity, were excluded in the experiments.

Treatment.

LPS derived from *Escherichia Coli* endotoxin (0111:B4, InvivoGen, USA, 1 mg/kg) was dissolved in normal saline and injected intraperitoneally. IL-1Ra (Amgen, Anakinra 100 mg/kg, Nederlands) was given subcutaneously immediately before LPS administration. Dose response curve from LPS or IL-1Ra was obtained from our pilot studies to provoke or to suppress moderate degree of microglia activation respectively. Control animals were injected with equivalent volumes (0.1 ml) of saline. Mice from each treatment group were randomly assigned for assessment of either cytokine response or cognitive behavior, in order to obviate possible confounding effects of behavioral testing on inflammatory markers [14].

Plasma Cytokine Measurement.

Blood was sampled transcardially after thoracotomy under terminal anesthesia 30 minutes, 2, 6, 12 hours and 1, 3, 7 days after experiments in the different cohorts and centrifuged at 3,600 rpm for 7 minutes at 4° C. Blood samples taken from animals without any interventions severed as controls. Plasma samples were stored at −20° C. for further analysis. Plasma cytokine and HMGB-1 were measured using commercially available ELISA kits from Biosource, CA and Shino-test Corporation, Japan, respectively. The sensitivities of the assays were <3 pg/ml for TNFα, <7 pg/ml for IL-1β, <3 pg/ml for IL-6 and 1 ng/ml for HMGB-1.

Quantitative Real Time PCR (qPCR).

The hippocampus was rapidly extracted under a dissecting microscope, placed in RNAlater solution (Applied Biosystems, Ambion) and stored at 4° C. Total RNA was extracted using RNeasy Kit (Qiagen) and quantified. The one-step qPCR was performed on a Rotor-Gene 6000(Corbett Life Science), using Assay-On-Demand premixed Taqmanprobe master mixes (Applied Biosystems). Each RNA sample was run in triplicate, and relative gene expression was calculated using the comparative threshold cycle $\Delta\Delta C_t$ and normalized to beta-actin (ACTB). Results are expressed as fold-increases relative to controls.

Immunohistochemistry (IHC).

Mice were euthanized and perfused transcardially with ice-cold heparinized 0.1M phosphate buffer solution (PBS) followed by 4% paraformaldehyde in 0.1M PBS at pH 7.4 (VWR International, UK). The brains were harvested and post-fixed in 4% paraformaldehyde in 0.1M PBS at 4° C. and cryoprotected in 0.1M PBS solutions containing 15% sucrose for 24 hours (VWR International, UK) and then 30% sucrose for a further 48 hours. Brain tissue was freeze-mounted in OCT embedding medium (VWR International, UK). The 25 µm thick coronal sections of the hippocampus were cut sequentially in groups of 6 and mounted on Superfrost® plus slides (Menzel-Glaser, Germany). The rat anti-mouse monoclonal antibody, anti-CD11b (low endotoxin, clone M1/70.15) in the concentration of 1:200 (Serotec, Oxford, UK) was used to label microglia. Visualization of immunoreactivity for CD11b was achieved using the avidin-biotin technique (Vector Labs, Cambridge, UK) and a goat anti-rat secondary antibody (Chemicon International, CA, USA) at a concentration of 1:200. A negative control omitting the primary antibody was performed in all experiments. Immunohistochemical photomicrographs were obtained with an Olympus BX-60 microscope and captured with a Zeiss KS-300 colour 3CCD camera. The assessment of staining, by an observer that was blinded to the interventional group, was based upon a 4-point categorical scale [15].

Behavioral Measurement (Conditioning).

The behavioral study was conducted using a dedicated conditioning chamber (Med Associates Inc., USA). Mice were trained and tested on separate days. LPS was injected within 30 minutes following training. The fear conditioning paradigm was used as previously described [16]. Three days after training, mice were returned to the same chamber in which training occurred (context), and freezing behavior was recorded. Freezing was defined as lack of movement except that required for respiration. Approximately 3 h later, freezing was recorded in a novel environment and in response to the cue (tone). The auditory cue was then presented for 3 min, and freezing scored again. Freezing scores for each subject were expressed as a percentage for each portion of the test. Memory for the context (contextual memory) for each subject was obtained by subtracting the percent freezing in the novel environment from that in the context.

Data Analysis.

Statistical analyses were performed using GraphPadPrism version 5.0a (GraphPad Software, San Diego, Calif.). The results are expressed as mean±SEM. Data were analyzed with analysis of variance followed by Newman-Keuls post hoc test wherever appropriate. For categorical data, non-parametric Kruskal-Wallis followed by Dunn's test was used. A $p<0.05$ was considered to be statistical significance.

Results

Endotoxin-Induced Cytokine Production is Modified by IL-1Ra and in IL-1R$^{-/-}$.

To investigate the effects of inflammation on cognitive function we measured systemic and central cytokines after LPS administration. TNFα release occurred very rapidly and transiently; after 30 minutes it was significantly increased (104.18±7.36 pg/ml), peaking at 2 hours and returning to normal at 6 hours post-injection (FIG. 9A; $p<0.01$, $p<0.001$ vs control). LPS evoked a robust systemic response that induced further cytokine release. Both IL-1β and IL-6 were significantly up regulated from 2 hours. IL-1β increased 4-fold and plasma levels continued to steadily increase until 24 hours (FIG. 9B; 73.49±5.42 pg/ml, $p<0.001$ vs control). IL-6 expression was highly elevated at 2 hours, decreasing at 6 hours but still significantly detectable at 24 hours compared to naïve animals (FIG. 9C; 134.37±8.43 pg/ml, $p<0.01$ vs control respectively). During this time, animals showed classic symptoms of sickness behavior (reduced motility, poor grooming, huddling, piloerection, back arching). Levels of HMGB-1 at 2, 6, and 12 hours post LPS were no different from baseline levels; a 1.5-fold increase was observed from 24 hours after LPS and remained elevated up to day 3 (FIG. 9D; 25.77±4.2 pg/ml, $p<0.01$, $p<0.001$ vs control). The systemic inflammatory response resolved after day 3 and all cytokine levels returned to baseline by day 7.

To assess the central inflammatory response to LPS we measured levels of IL-1 and IL-6 mRNA expression in the hippocampus. We noted a 6.5-fold increase in IL-1β mRNA expression and a 15-fold increase in IL-6 in the hippocampus at 6 hours after LPS injection (FIG. 9E,F; $p<0.001$ vs control respectively). In both cases the increased transcription returned to normal values by 24 hours. The increase in IL-1β both in plasma and in the hippocampus led us to investigate whether blocking the IL-1 receptor could ameliorate the signs of LPS-associated cognitive dysfunction. A single preemptive dose of IL-1 Ra was able to significantly reduce plasma levels of IL-1β at 6 and 24 hours (FIG. 10A, 32.7±5.45 pg/ml, 6.2±1.03 pg/ml, $p<0.01$ and $p<0.001$ vs LPS respectively). Similarly, levels of IL-6 were also reduced at the same time-points (FIG. 10B; 91.02±15.17 pg/ml, 14.05±2.34 pg/ml, $p<0.001$, $p<0.001$ vs LPS respectively). Interestingly, IL-1Ra treatment had no effects on HMGB-1 levels, which maintained a similar pattern at that seen after LPS injection in the absence of IL-1Ra (FIG. 10C). Corroboration of these data was achieved by injecting IL-1R$^{-/-}$ animals with the same dose of LPS and measuring cytokine expression in plasma. At 24 hours, time characterized by increased cytokines and clear sickness behavior, levels of IL-1β and IL-6 were comparable to the wild type mice that received IL-1Ra treatment (FIG. 10A,B; $p<0.0001$, $p<0.001$ vs LPS respectively). However, upon measurement of HMGB-1 in IL-1R$^{-/-}$, no differences were reported compared to either WT or IL-1Ra treated animals (FIG. 10C).

LPS-Induced Microglial Activation is Modified by IL-1Ra and Absent in IL-1R$^{-/-}$.

The hippocampal transcriptome findings prompted interest for other possible markers of neuroinflammation. Microglia, the resident immunocompetent cells of the CNS, were significantly up regulated following LPS injection. Minimal immunoreactivity was reported in naïve animals in which cells maintained small cell bodies with thin and long ramified pseudopodia (FIG. 11A). Resting microglia shifted to a "reactive profile" after LPS exposure, acquiring an amoeboid morphology with hypertrophy of the cell body and retraction of the pseudopodia. Reactive microglia displayed morphological changes including increased cell body dimensions, shortened and clumpy processes with higher levels of CD11b immunoreactivity compared to naïve animals. Microglial activation was reported at days 1 and 3 post exposure (FIG. 11B,C; $p<0.01$, $p<0.05$ vs control), returning to the baseline resting state by day 7. Pre-treatment with IL-1Ra effectively reduced the number of reactive microglia at days 1 and 3 (FIG. 11E,F), with no changes at day 7. In order to corroborate these findings, we repeated the experiment using IL-1R$^{-/-}$ animals and exposing them to LPS. No microglial activation was noted in LPS treated IL-1R$^{-/-}$ mice (FIG. 11G,H,I).

Hippocampal-Dependent Cognitive Dysfunction Following LPS is Ameliorated by IL-1 Blockade.

To relate the inflammatory response to memory functioning, we used trace fear conditioning in which mice are trained to associate a tone with a noxious stimulation (foot shock). The brief gap between the tone termination and the shock onset allows assessment of hippocampal integrity [16]. The high level of freezing seen in the naïve animals is indicative of good learning and memory retention. Contextual fear response shows a reduced immobility (freezing) at day 3, revealing and hippocampal-dependent memory impairment (FIG. 12; p<0.005 vs naïve trained). Pre-treatment with IL-1Ra significantly ameliorated this cognitive dysfunction (FIG. 12; p<0.05 vs LPS).

Discussion

These data show that a sustained inflammatory challenge leads to neuroinflammation, microglial activation and hippocampal-mediated cognitive dysfunction. By blocking the IL-1 receptor, the feed-forward process that amplifies the inflammatory cascade is attenuated thereby reducing microglial activation and reversing the behavioral abnormality after endotoxemia.

Peripheral and Central Cytokines Contribute to the Inflammatory Milieu in Sickness Behavior.

Cytokines play an important role in mediating the inflammatory response after infection or aseptic traumatic injury. The innate immunity is rapidly triggered after LPS, primarily via activation of toll-like receptor 4, TLR-4 [17]. Activation of TLR-4 induces a multitude of pro-inflammatory cytokines via activation of transcription factors, NFκB [18]. This prompt response provides a favorable environment for the synthesis and up regulation of both IL-1β and IL-6, which together contribute to the perpetuation of the inflammatory challenge. Also the rapid increase in TNF-α following LPS, which is reported as present already after 30 minutes, promotes synthesis of other cytokines and the initiation of the acute-phase response. Systemic cytokines, including IL-1β, can bind receptors and translocate through the intact blood-brain barrier (BBB) [19]. Neural afferents are known to be a fast and reliable pathway in the immune-to-brain signaling. Vagal-mediated signaling can rapidly induce brain cytokines and manifest the classic symptoms of the acute phase response, including neuroinflammation [20]. As we have reported a significant increase in both IL-1 and IL-6 mRNA transcription at 6 hours in the hippocampus, the neuronal route may be the likely pathway to trigger the early activation of these genes and the initial changes in the CNS. Vagotomy was previously shown to partially attenuate sickness behavior both after LPS and IL-1β administration [21], but not in the context of hippocampal-dependent cognitive dysfunction.

Reactive Microglia in the Hippocampus Interfere with Memory Processing.

Within the brain, cytokines interact with microglia cells. Pro-inflammatory cytokines can directly interact with many of the pattern recognition receptors (PRRs) expressed on the surface of these cells [22]. Upon activation, microglia exhibit discernible morphologic changes and secrete cytokines, reactive oxygen species (ROS), excitotoxins (such as calcium and glutamate) and neurotoxins such as amyloid-β [23]. Activated microglia also inhibit neurogenesis in the hippocampus following endotoxemia, thereby exacerbating the extent of injury on memory processing [24]. To assess memory retention we used trace fear conditioning in which mice are trained to associate a foot shock with a given environment or tone [25]. The extent to which an animal freezes to a context is largely dependent on the hippocampus [26]. Hippocampal-dependent memory impairment was evident after 3 days post-LPS. Residual inflammation, primarily via reactive microglia, is possibly associated with this second phase behavioral abnormality. At these time points, levels of HMGB-1 were also elevated and prompted us to further investigate the role of these factors in the development of cognitive dysfunction.

Targeting IL-1 Ameliorates the Cognitive Abnormality by Reducing Microglia but does not Affect HMGB1.

IL-1β has a pivotal role in sustaining the neuroinflammatory response and closely interacts with memory processing and long-term potentiation [27, 28]. Self-regulation and inhibition of IL-1β is normally achieved with the neutralizing action of endogenous IL-1Ra, which directly competes for binding to the receptor [29, 30]. Transcription of endogenous IL-1 Ra would normally occur temporally delayed from the synthesis of IL-1, thus following pharmacological intervention we aimed to block the receptor a priori impeding binding and limiting the damage mediated by the effector molecule. When the IL-1 receptor is disabled, either blocked pharmacologically (IL-1Ra) or by genetic intervention (IL-1R$^{-/-}$), the inflammatory response is not sustained as reflected by lower cytokine release and microglia activation, thus ameliorating the cognitive dysfunction as reported here. Treatment with IL-1Ra provides a significant improvement in cognitive dysfunction, confirming the crucial role of IL-1β in memory processes and behavior. Although there was a temporal correlation between microglia activation and late-release of HMGB-1, neither IL-1Ra nor IL-1R$^{-/-}$ changed levels of in this cytokine. This evidence supports the notion that blocking IL-1 is sufficient to reduce the microglia activation and ameliorate the memory abnormality. Other receptors may be involved in sustaining this inflammatory challenge; for example HMGB-1 has been shown to activate TLRs and receptor for advanced glycation end-products (RAGE) and it has been reported as a key late pro-inflammatory mediator in sepsis, with considerable pathological potential [11, 31].

Some limitations of our study must be pointed out. Since IL-1Ra is able to translocate directly into the brain [32], we are unable to discriminate whether peripheral cytokines and/or de-novo production in the CNS account for this cognitive dysfunction. Also, recently it has been shown that peripheral monocytes can enter the brain causing sickness behavior. This process strongly relies on TNF-α signaling, especially in activating microglia and recruiting active monocytes into the CNS [33]. In this study we cannot determine the nature of the microgliosis, whether they are infiltrated macrophages that crossed the BBB or actual microglia.

Conclusion

The beneficial effects on cognition reported in this study by targeting IL-1, preemptively, are encouraging. However, it is not possible to extrapolate these benefits to the setting of cognitive dysfunction that accompanies severe sepsis with multiple organ failure. In that clinical scenario there are complex inflammatory responses that are difficult to reverse [34]. Clinical trials targeting IL-1 have been unconvincing in improving mortality rate, especially in sepsis [35]. In this attempt to untangle the complexity of this condition, anti-IL-1 therapy appears to be able to ameliorate the associated cognitive dysfunction, independently of other mechanisms. Inflammation clearly plays a pivotal role in mediating physiological as well as behavioral changes after LPS-exposure.

Further studies are needed to ascertain whether selective targeting of other cytokine receptors can effectively prevent or ameliorate both the degree and length of cognitive decline.

Key Messages

Neuroinflammation plays a pivotal role in mediating physiological and behavioral changes after LPS Up-regulation of microglia and HMGB-1 correlates in a temporal fashion with the cognitive dysfunction Blocking IL-1 does not affect HMGB-1 release, however it reduces microglia activation reversing the behavioral abnormality In the absence of IL-1, HMGB-1 is insufficient to sustain hippocampal neuroinflammation and the attendant cognitive dysfunction. Further studies are required to investigate the potential benefit of anti-cytokine therapy in the ICU.

Abbreviations

High-mobility group box 1 (HMGB-1), interleukin (IL), lipopolysaccharide (LPS), toll-like receptor (TLR), tumor necrosis factor-α (TNFα)

REFERENCES

1. Dantzer R: Cytokine-induced sickness behaviour: a neuroimmune response to activation of innate immunity. *Eur J Pharmacol* 2004, 500(1-3):399-411.
2. Annane D: Hippocampus: a future target for sepsis treatment *Intensive Care Med* 2009, 35(4):585-586.
3. Pugh C R, Kumagawa K, Fleshner M, Watkins L R, Maier S F, Rudy J W: Selective effects of peripheral lipopolysaccharide administration on contextual and auditory-cue fear conditioning. *Brain Behav Immun* 1998, 12(3):212-229.
4. Dinarello C A: Biologic basis for interleukin-1 in disease. *Blood* 1996, 87(6):2095-2147.
5. Murray C A, Lynch M A: Evidence that increased hippocampal expression of the cytokine interleukin-1 beta is a common trigger for age- and stress-induced impairments in long-term potentiation. *J Neurosci* 1998, 18(8): 2974-2981.
6. Parnet P, Amindari S, Wu C, Brunke-Reese D, Goujon E, Weyhenmeyer J A, Dantzer R, Kelley K W: Expression of type I and type II interleukin-1 receptors in mouse brain. *Brain Res Mol Brain Res* 1994, 27(1):63-70.
7. Gemma C, Fister M, Hudson C, Bickford P C: Improvement of memory for context by inhibition of caspase-1 in aged rats. *Eur J Neurosci* 2005, 22(7):1751-1756.
8. Rachal Pugh C, Fleshner M, Watkins L R, Maier S F, Rudy J W: The immune system and memory consolidation: a role for the cytokine IL-1beta. *Neurosci Biobehav Rev* 2001, 25(1):29-41.
9. Chen J, Buchanan J B, Sparkman N L, Godbout J P, Freund G G, Johnson R W: Neuroinflammation and disruption in working memory in aged mice after acute stimulation of the peripheral innate immune system. *Brain Behav Immun* 2008, 22(3):301-311.
10. Allan S M, Tyrrell P J, Rothwell N J: Interleukin-1 and neuronal injury. *Nat Rev Immunol* 2005, 5(8):629-640.
11. Wang H, Bloom O, Zhang M, Vishnubhakat J M, Ombrellino M, Che J, Frazier A, Yang H, Ivanova S, Borovikova L et al: HMG-1 as a late mediator of endotoxin lethality in mice. *Science* 1999, 285(5425):248-251.
12. Gordon S M, Jackson J C, Ely E W, Burger C, Hopkins R O: Clinical identification of cognitive impairment in ICU survivors: insights for intensivists. *Intensive Care Med* 2004, 30(11):1997-2008.
13. Labow M, Shuster D, Zetterstrom M, Nunes P, Terry R, Cullinan E B, Bartfai T, Solorzano C, Moldawer L L, Chizzonite R et al: Absence of IL-1 signaling and reduced inflammatory response in IL-1 type I receptor-deficient mice. *J Immunol* 1997, 159(5): 2452-2461.
14. Nguyen K T, Deak T, Owens S M, Kohno T, Fleshner M, Watkins L R, Maier S F: Exposure to acute stress induces brain interleukin-1beta protein in the rat. *J Neurosci* 1998, 18(6):2239-2246.
15. Colburn R W, DeLeo J A, Rickman A J, Yeager M P, Kwon P, Hickey W F: Dissociation of microglial activation and neuropathic pain behaviors following peripheral nerve injury in the rat. *J Neuroimmunol* 1997, 79(2):163-175.
16. Comery T A, Martone R L, Aschmies S, Atchison K P, Diamantidis G, Gong X, Zhou H, Kreft A F, Pangalos M N, Sonnenberg-Reines J et al: Acute gamma-secretase inhibition improves contextual fear conditioning in the Tg2576 mouse model of Alzheimer's disease. *J Neurosci* 2005, 25(39):8898-8902.
17. Hoshino K, Takeuchi O, Kawai T, Sanjo H, Ogawa T, Takeda Y, Takeda K, Akira S: Cutting edge: Toll-like receptor 4 (TLR4)-deficient mice are hyporesponsive to lipopolysaccharide: evidence for TLR4 as the Lps gene product. *J Immunol* 1999, 162(7):3749-3752.
18. Andreakos E, Sacre S M, Smith C, Lundberg A, Kiriakidis S, Stonehouse T, Monaco C, Feldmann M, Foxwell B M: Distinct pathways of LPS-induced N F-kappa B activation and cytokine production in human myeloid and nonmyeloid cells defined by selective utilization of MyD88 and Mal/TIRAP. *Blood* 2004, 103(6): 2229-2237.
19. Van Dam A M, Brouns M, Man A H W, Berkenbosch F: Immunocytochemical detection of prostaglandin E2 in microvasculature and in neurons of rat brain after administration of bacterial endotoxin. *Brain Res* 1993, 613(2): 331-336.
20. Dantzer R: How do cytokines say hello to the brain? Neural versus humoral mediation. *Eur Cytokine Netw* 1994, 5(3):271-273.
21. Hansen M K, Taishi P, Chen Z, Krueger J M: Vagotomy blocks the induction of interleukin-1beta (IL-1beta) mRNA in the brain of rats in response to systemic IL-1beta. *J Neurosci* 1998, 18(6):2247-2253.
22. Aloisi F: Immune function of microglia. *Glia* 2001, 36(2):165-179.
23. Hanisch U K, Kettenmann H: Microglia: active sensor and versatile effector cells in the normal and pathologic brain. *Nat Neurosci* 2007, 10(11):1387-1394.
24. Monje M L, Toda H, Palmer T D: Inflammatory blockade restores adult hippocampal neurogenesis. *Science* 2003, 302(5651): 1760-1765.
25. Fanselow M S: Conditioned and unconditional components of post-shock freezing. Pavlov *J Biol Sci* 1980, 15(4):177-182.
26. Maren S, Aharonov G, Fanselow M S: Neurotoxic lesions of the dorsal hippocampus and Pavlovian fear conditioning in rats. *Behav Brain Res* 1997, 88(2):261-274.
27. Vereker E, Campbell V, Roche E, McEntee E, Lynch M A: Lipopolysaccharide inhibits long term potentiation in the rat dentate gyrus by activating caspase-1. *J Biol Chem* 2000, 275(34):26252-26258.
28. Barrientos R M, Higgins E A, Sprunger D B, Watkins L R, Rudy J W, Maier S F: Memory for context is impaired by a post context exposure injection of interleukin-1 beta into dorsal hippocampus. *Behav Brain Res* 2002, 134(1-2):291-298.
29. Arend W P: Interleukin 1 receptor antagonist. A new member of the interleukin 1 family. *J Clin Invest* 1991, 88(5):1445-1451.
30. Dinarello C A: Blocking IL-1 in systemic inflammation. *J Exp Med* 2005, 201(9):1355-1359.
31. van Zoelen M A, Yang H, Florquin S, Meijers J C, Akira S, Arnold B, Nawroth P P, Bierhaus A, Tracey K J, Poll T: Role of toll-like receptors 2 and 4, and the receptor for advanced glycation end products in high-mobility group box 1-induced inflammation in vivo. *Shock* 2009, 31(3):280-284.
32. Skinner R A, Gibson R M, Rothwell N J, Pinteaux E, Penny J I: Transport of interleukin-1 across cerebromicrovascular endothelial cells. *Br J Pharmacol* 2009, 156(7):1115-1123.
33. D'Mello C, Le T, Swain M G: Cerebral microglia recruit monocytes into the brain in response to tumor necrosis factoralpha signaling during peripheral organ inflammation. *J Neurosci* 2009, 29(7):2089-2102.
34. Riedemann N C, Guo R F, Ward P A: Novel strategies for the treatment of sepsis. *Nat Med* 2003, 9(5):517-524.
35. Marshall J C: Such stuff as dreams are made on: mediator-directed therapy in sepsis. *Nat Rev Drug Discov* 2003, 2(5):391-405.

Example 3: Anti-Cytokine Therapy for Postoperative Cognitive Dysfunction

Introduction

Postoperative cognitive dysfunction (POCD) is a well-described complication that follows different surgical interventions, affecting primarily the elderly (1). Etiology and mechanisms underlying this phenomenon still remains elusive and not yet fully understood. With surgical operations already exceeding 230 million worldwide and the escalating surgical projections for the aging population, POCD will be an important complication with a significant burden on patients and health care management (2-4).

POCD is associated with poor short-term and long-term outcomes such as increased risk of mortality and comorbidities, including the possibility of permanent dementia and further neurodegeneration (5, 6). Multiple factors (patient-related, perioperative care and surgery) are thought to modify the risk of developing POCD; to date clinical studies have not revealed the mechanisms for cognitive disturbances (7). Exploitation of the clinical knowledge into animal models provides novel insights into the risk factors and mechanisms in this condition (8, 9). We postulated that targeting tumor necrosis factor-α (TNFα) can block the perpetuation of the inflammatory challenge and ameliorate the cognitive dysfunction.

Methods

Animals:

All the experiments were conducted under the UK Home Office approved license. Wild type C57BL/6 male mice (Harlan, UK) 12-14 weeks old were used. MyD88$^{-/-}$(10) and TLR4$^{-/-}$ were bred in house on a C57BL/6 background and age-matched to wild type counterparts. All the animals were checked on a daily basis and if they evidenced poor grooming, huddling, piloerection, weight loss, back arching and abnormal activity, they were eliminated from further consideration.

Surgery:

Mice were subjected to an open tibial fracture, stripped of periosteum with intramedullary fixation, under aseptic conditions and general anaesthesia with inhaled isoflurane (MAC 1.5) and analgesia with buprenorphine as previously described (11). Untreated animals served as naïve controls. TNF neutralizing antibody (clone TN3, Sigma, UK, 100 pg in 0.1 ml/volume) was dissolved in normal saline and injected 18 hours before surgery. LPS derived from *Escherichia Coli* endotoxin (0111:B4, InvivoGen, USA, 1 mg/kg) was dissolved in normal saline and injected intraperitoneally to serve as positive control (data not shown).

Cytokine Analyses:

Systemic and hippocampal IL-1β was measured by ELISA (Bender Medsystem, CA; 1.2 pg/ml of sensitivity), as previously described (12).

Immunohistochemistry:

Fixed brains were collected for immunohistochemical DAB staining for microglia activation using CD11 b and scored as previously described (13).

Behavioral Measurement (Conditioning).

The behavioral study was conducted using a dedicated conditioning chamber (Med Associates Inc., USA). Mice were trained and tested on separate days. The fear conditioning paradigm was used as previously described (14). Three days after training, mice were returned to the same chamber in which training occurred (context), and freezing behavior was recorded. Freezing was defined as lack of movement except that required for respiration. Freezing scores for each subject were expressed as a percentage for each portion of the test. Memory for the context (contextual memory) for each subject was obtained by subtracting the percent freezing in the novel environment from that in the context.

Data Analysis.

Statistical analyses were performed using GraphPadPrism (GraphPad Software, San Diego, Calif.). The results are expressed as mean±SEM. Data were analyzed with analysis of variance followed by Newman-Keuls post hoc test wherever appropriate. For categorical data, non-parametric Kruskal-Wallis followed by Dunn's test was used. A $p<0.05$ was considered to be statistical significance.

Results

To investigate the effects of inflammation on surgery-induced cognitive abnormalities we targeted TNFα as the putative initiator of this process. A positive trend in systemic TNFα, from 30 to 60 minutes, was observed following tibial surgery (see FIG. 13).

Preemptive administration of anti-TNFα effectively reduced the amount of systemic IL-1 both at 6 hours and 24 hours following tibia surgery ($p<0.01$ and $p<0.001$ vs surgery only respectively). To corroborate the findings and ascertain the specificity of TNF, we delayed the injection of the antibody and levels of IL-1β remained unaffected (see FIG. 14A). To better understand the effects of the TNFα blockade on other cytokines we also measured levels of IL-6 as downstream products from IL-1 receptor. Prophylaxis with anti-TNFα reduced systemic levels of IL-6 both at 6 and 24 hours ($p<0.01$ and $p<0.05$ vs surgery only respectively). If the TNFα blockade was delayed, no effects were observed on IL-6 similarly to IL-1 (see FIG. 14B). In order to correlate the systemic changes with central markers of inflammation, we measured levels of IL-1β and assessed microglia activation in the hippocampus. Prophylaxis with anti-TNF significantly reduced the levels of hippocampal IL-1β compared to untreated animals (see FIG. 14C, $p<0.01$). Microglia, the resident immunocompetent cells of the CNS, shifted their state to a "reactive profile" after surgery, acquiring an amoeboid morphology with hypertrophy of the cell body and retraction of the pseudopodia (see FIG. 14E). Minimal immunoreactivity was reported in naïve animals in which cells maintained small cell bodies with thin and long ramified pseudopodia (see FIG. 14E). Treatment with anti-TNF reduced the amount of microgliosis seen after surgery (see FIG. 14F, G; $p<0.01$ vs surgery). To relate the inflammatory response to memory functioning, we used trace fear conditioning (TFC) in which mice are trained to associate a tone with a noxious stimulation. The brief gap between the tone termination and the shock onset allows assessment of hippocampal integrity (15). The high level of freezing seen in the naïve animals is indicative of good learning and memory retention. No differences in freezing time were reported between groups during training (data not shown). Contextual fear response however shows a reduced immobility (freezing) at postoperative day 3, revealing hippocampal-dependent memory impairment (see FIG. 14H; $p<0.05$ vs naïve trained). Pre-treatment with anti-TNF significantly ameliorated this cognitive dysfunction (see FIG. 14H; $p<0.05$ vs surgery). Also, administration of anti-TNF immediately after surgery still under effects of general anesthesia, provided a similar amelioration (data not shown).

The effects of anti-TNFα prophylaxis, in particular on IL-1, provided further insights into the possible role of IL-1 and non-TNFα signalling in POCD-associated behavior. Reduction of systemic inflammation both at 6 and 24 hours was observed in MyD88$^{-/-}$ (see FIG. 15A, B), reaching similar values after prophylaxis in WT animals. In order to correlate the systemic changes with neuroinflammation and eventual behavioral abnormality, we assessed hippocampal IL-1β and microglia activation. No signs of neuroinflammation were reported in MyD88$^{-/-}$ following surgery (see FIG. 15C, F). In order to understand the role of MyD88$^{-/-}$ in POCD-associated behaviour we used TFC to assess memory retention following surgery. Contextual retrieval task revealed no significant changes in freezing behavior comparing naïve MyD88$^{-/-}$ to animals receiving tibia surgery (see FIG. 15G). Despite the significant reduction in systemic IL-1 both following anti-TNFα prophylaxis and using MyD88$^{-/-}$, the IL-1 response was not obliterated. This led us to further investigate whether a putative synergistic interaction between TNFα and IL-1β could account for sustaining the response. When MyD88$^{-/-}$ were treated with preemptive anti-TNFα, the response to IL-1β and IL-6 was completely eliminated (see FIG. 15H, I; $p<0.001$, $p<0.01$ vs surgery respectively).

To further understand the involvement of MyD88-dependent signaling in POCD, we investigated the inflammatory response in TLR4$^{-/-}$. Only a subtle reduction in plasma levels of IL-1β and IL-6 was observed at 6 hours following surgery, but by 24 hours pro-inflammatory cytokines were unchanged from WT. The systemic response was fully abrogated following treatment with anti-TNFα, similarly to what observed after prophylaxis in MyD88$^{-/-}$ (see FIG. 16A, B). Furthermore, administration of anti-TNFα resolved the neuroinflammatory signs present in TLR4' following surgery, including hippocampal IL-1β (see FIG. 16C, $p<0.01$ vs ab) and microglial activation (see FIG. 16G, $p<0.01$ vs naïve and ab). To corroborate the importance of this inflammatory challenge with POCD-associated behavior, TFC revealed a clear hippocampal impairment following surgery in TLR4, similarly to WT (see FIG. 16H, $p<0.05$ vs naive).

Discussion

These data demonstrate that anti-TNFα monoclonal antibody reduces the inflammatory burden following surgery, through the elaboration of IL-1β. The importance of IL-1β in POCD can be seen from Example 1 above. Herein we demonstrate that preemptive targeting of TNFα as an early marker during post-surgical inflammation suppresses generation of IL-1, strengthening the role of cytokines in the etiology of POCD. In order to define the origin of the IL-1 response, we also explored MyD88- and TL4-dependent signaling.

Given the limited penetration of the antibody into the brain, our data suggest a pivotal role for the initial peripheral response in the development of neuroinflammation and POCD-associated behavioural changes. Reduction of IL-1β through TNFα improves behavioral performance, suggesting a key role of inflammation in the development of behavioral abnormalities and further proving the determinant role of IL-1 in memory processes (16, 17).

Due to the recent discoveries of independent MyD88 pathways in the IL-1 signaling (18), we investigated the response following surgery in animals lacking expression of this key adaptor molecule. MyD88$^{-/-}$ showed a reduction, albeit not complete, in IL-1β. Dampening of the inflammatory challenge appears to be sufficient to provide benefit POCD-associated behavior following surgery in MyD88. This suggests a threshold effect in which a certain level of IL-1 is required to trigger enough neuroinflammation to impact on memory functioning resulting in the behavioral changes. Combination of anti-TNFα prophylaxis to MyD88$^{-/-}$ was able to completely abrogate the response to IL-1β. The results from the TFC also suggest that the elimination of either cytokines will diminish cognitive dysfunction following surgical trauma (i.e. threshold effect).

The demonstration of the importance of MyD88 signaling in POCD yielded to further investigate whether targeting of specific receptors could ameliorate POCD symptoms. Due to the findings on the involvement of TLR4 during sterile inflammation and trauma (fracture) (19), we sought to look at the inflammatory response in TLR4$^{-/-}$. Both IL-1β response and cognitive dysfunction after surgical stimulation was not eliminated. However, anti-TNFα prophylaxis was able to reduce the inflammatory challenge in TLR4$^{-/-}$, further proving the key role of TNFα in the generation of IL-1β through a MyD88 independent pathway following surgery.

Herein we provide evidence for IL-1β working through MyD88 mechanism but, in addition, targeting of TNFα significantly ameliorates the cognitive dysfunction after surgery by reducing IL-1β. Therapy with TNF inhibitors already offers beneficial effects in other settings such as rheumatoid arthritis (20). Following a single preemptive administration we reported no evidences of infection or sickness behavior in this study, thus overcoming some of the limitations of these agents in facilitating postoperative complications, in particular infections.

REFERENCES

1. Moller J T, Cluitmans P, Rasmussen L S, Houx P, Rasmussen H, Canet J, et al. Long-term postoperative cognitive dysfunction in the elderly ISPOCD1 study. ISPOCD investigators. International Study of Post-Operative Cognitive Dysfunction. Lancet. 1998 Mar. 21; 351(9106):857-61.
2. Weiser T G, Regenbogen S E, Thompson K D, Haynes A B, Lipsitz S R, Berry W R, et al. An estimation of the global volume of surgery: a modelling strategy based on available data. Lancet. 2008 Jul. 12; 372(9633):139-44.
3. Etzioni D A, Liu J H, Maggard M A, Ko C Y. The aging population and its impact on the surgery workforce. Ann Surg. 2003 August; 238(2):170-7.
4. Gao L, Taha R, Gauvin D, Othmen L B, Wang Y, Blaise G. Postoperative cognitive dysfunction after cardiac surgery. Chest. 2005 November; 128(5):3664-70.
5. Francis J, Kapoor W N. Prognosis after hospital discharge of older medical patients with delirium. J Am Geriatr Soc. 1992 June; 40(6):601-6.
6. Steinmetz J, Christensen K B, Lund T, Lohse N, Rasmussen L S. Long-term consequences of postoperative cognitive dysfunction. Anesthesiology. 2009 March; 110(3):548-55.
7. Newman S, Stygall J, Hirani S, Shaefi S, Maze M. Postoperative cognitive dysfunction after noncardiac surgery: a systematic review. Anesthesiology. 2007 March; 106(3):572-90.
8. Wan Y, Xu J, Ma D, Zeng Y, Cibelli M, Maze M. Postoperative impairment of cognitive function in rats: a possible role for cytokine-mediated inflammation in the hippocampus. Anesthesiology. 2007 March; 106(3):436-43.
9. Rosczyk H A, Sparkman N L, Johnson R W. Neuroinflammation and cognitive function in aged mice following minor surgery. Exp Gerontol. 2008 September; 43(9):840-6.
10. Adachi O, Kawai T, Takeda K, Matsumoto M, Tsutsui H, Sakagami M, et al. Targeted disruption of the MyD88 gene results in loss of IL-1- and IL-18-mediated function. Immunity. 1998 July; 9(1):143-50.
11. Harry L E, Sandison A, Paleolog E M, Hansen U, Pearse M F, Nanchahal J. Comparison of the healing of open tibial fractures covered with either muscle or fasciocutaneous tissue in a murine model. J Orthop Res. 2008 September; 26(9):1238-44.
12. Nguyen K T, Deak T, Owens S M, Kohno T, Fleshner M, Watkins L R, et al. Exposure to acute stress induces brain interleukin-1beta protein in the rat. J Neurosci. 1998 Mar. 15; 18(6):2239-46.
13. Colburn R W, DeLeo J A, Rickman A J, Yeager M P, Kwon P, Hickey W F. Dissociation of microglial activation and neuropathic pain behaviors following peripheral nerve injury in the rat. J Neuroimmunol. 1997 November; 79(2):163-75.
14. Comery T A, Martone R L, Aschmies S, Atchison K P, Diamantidis G, Gong X, et al. Acute gamma-secretase inhibition improves contextual fear conditioning in the Tg2576 mouse model of Alzheimer's disease. J Neurosci. 2005 Sep. 28; 25(39):8898-902.
15. Chowdhury N, Quinn J J, Fanselow M S. Dorsal hippocampus involvement in trace fear conditioning with long, but not short, trace intervals in mice. Behav Neurosci. 2005 October; 119(5):1396-402.
16. Pugh C R, Nguyen K T, Gonyea J L, Fleshner M, Wakins L R, Maier S F, et al. Role of interleukin-1 beta in impairment of contextual fear conditioning caused by social isolation. Behav Brain Res. 1999 December; 106(1-2):109-18.
17. Barrientos R M, Higgins E A, Sprunger D B, Watkins L R, Rudy J W, Maier S F. Memory for context is impaired by a post context exposure injection of interleukin-1 beta into dorsal hippocampus. Behav Brain Res. 2002 Aug. 21; 134(1-2):291-8.
18. Kenny E F, O'Neill L A. Signalling adaptors used by Toll-like receptors: an update. Cytokine. 2008 September; 43(3):342-9.
19. Levy R M, Prince J M, Yang R, Mollen K P, Liao H, Watson G A, et al. Systemic inflammation and remote organ damage following bilateral femur fracture requires Toll-like receptor 4. Am J Physiol Regul Integr Comp Physiol. 2006 October; 291(4):R970-6.
20. Taylor P C, Feldmann M. Anti-TNF biologic agents: still the therapy of choice for rheumatoid arthritis. Nat Rev Rheumatol. 2009 October; 5(10):578-82.
Ely, E. W., S. Gautam, R. Margolin, J. Francis, L. May, T. Speroff, B. Truman, R. Dittus, R. Bernard and S. K. Inouye (2001). "The impact of delirium in the intensive care unit on hospital length of stay." *Intensive Care Med* 27(12): 1892-900.
Ely, E. W., A. Shintani, B. Truman, T. Speroff, S. M. Gordon, F. E. Harrell, Jr., S. K. Inouye, G. R. Bernard and R. S. Dittus (2004). "Delirium as a predictor of mortality in mechanically ventilated patients in the intensive care unit." *JAMA* 291(14): 1753-62.
Milbrandt, E. B., S. Deppen, P. L. Harrison, A. K. Shintani, T. Speroff, R. A. Stiles, B. Truman, G. R. Bernard, R. S. Dittus and E. W. Ely (2004). "Costs associated with delirium in mechanically ventilated patients." *Crit Care Med* 32(4): 955-62.

Example 4: The Interactions Between Postoperative Infection, Surgery, and Inflammation in Post-Operative Cognitive Dysfunction Background:

Recovery from surgery may be complicated by postoperative cognitive dysfunction (POCD), especially in high-risk patients [1]. Postoperative complications, for example infection, have been associated with higher incidence of POCD although the mechanisms governing the interaction in the pathogenesis of POCD are not known [2]. Recently, neuroinflammation has been correlated with cognitive decline [3,4]. In this study we sought to understand the effect of postoperative lipopolysaccharide (LPS) on inflammation and POCD-associated behavior after orthopedic surgery.

Methods:

Adult C56BL/6J male mice were randomly assigned into groups that were: 1) untreated (naïve) animals; 2) tibial fracture under GA and analgesia; 3) 24 h following tibial surgery, i.p. injection of LPS (1 mg/kg) 4) LPS injection only. Separate cohorts of mice per group were assessed for inflammatory markers (plasma cytokines and microglial activation), or hippocampal-dependent memory using trace fear conditioning (TFC).

Results:

TFC assessment at three days after surgery and LPS revealed a significant reduction in freezing behavior compared to both naïve littermates and animals undergoing surgery only, without complication (p<0.05 vs surgery). Up-regulation of systemic cytokines is usually self-limited to the initial 24 h; however, postsurgical administration of LPS up-regulated plasma levels of IL-1☐ for 72 h following intervention (p<0.001 vs control). In the hippocampus we reported higher degree of reactive microgliosis (CD11b) in animals treated with LPS compared to surgery or naïve; microgliosis was reported up to postoperative day 7 in the postsurgical LPS group (p<0.05).

Conclusion:

Cytokines are pivotal mediators in triggering and sustaining cognitive dysfunctions following aseptic inflammation following tibial fracture. Supervention of infection following aseptic trauma exaggerates inflammation and thereby exacerbates POCD. The individual contributions and their convergence on the inflammatory pathways will help define potential targets for intervention.

REFERENCES

1. Moller J. T. et al, Lancet 1998; 351:857-61; 2. Gao L. et al, Chest 2005; 128:3664-70; 3. Wan Y. et al, Anesthesiology 2007; 106:436-43; 4. Rosczyk H. A. et al, Exp Gerontol 2008; 43:840-46

REFERENCES FOR TNF ALPHA ANTAGONISTS

Furst, D. E., Schiff, M. H, Fleischmann, R. M., Strand, V., Birbara, C. A., Compagnone, D., Fischkoff, S. A., Chartash, E. K. (2003) Adalimumab, a fully human anti-tumor necrosis factor-alpha monoclonal antibody, and concomitant standard anti-rheumatic therapy for the treatment of rheumatoid arthritis: Results of STAR (Safety Trial of Adalimumab in Rheumatoid Arthritis). *J. Rheumatol.* 30(12): 2563-2571.

Van de Putte, L. B. A., Rau, R., Breedveld, F. C., Kalden, J. R., Malaise, M. G., van Riel, P. Schattenkirchner, M., Emery, P., Burmester, G. R., Zeidler, H., Moutsopoulos, H. M., Beck, K., Kupper, H. (2003) Efficacy and safety of teh fully human anti-tumour necrosis factor alpha monoclonal antibody adalimumab (D2E7) in DMARD refractory patients with rheumatoid arthritis: a 12 week, phase II study. *Annals of the Rheumatic Diseases.* 62(12): 1168-1177.

Moreland, L. W., Baumgartner, S. W., Schiff, M. H., Tindall, E. A., Fleischmann, R. M., Weaver, A. L., Ettlinger, R. E., Cohen, S., Koopman, W. J., Mohler, K., Widmer, M. B., Blosch, C. M. (1997) Treatment of rheumatoid arthritis with a recombinant human tumor necrosis factor receptor (p75)-Fc fusion protein. *N. Enql. J. Med.* 337(3): 141-7.

Knight, D. M., Trinh, H., Le, J., Siegel, S., Shealy, D., McDonough, M., Scallon, B., Moore, M. A., Vilcek, J., Daddona, P. and Ghrayeb, J. (1993) Construction and initial characterization of a mouse-human chimeric anti-TNF antibody. *Mol. Immunol.* 30(16): 1443-53.

Tanaka, S., Nagashima, T., Hori, T. (1998) In vitro inhibition of binding of tumor necrosis factor (TNF)-alpha by monoclonal antibody to TNF receptor on glioma cell and monocyte. *Neuroloqia Medico-Chirurqica* 38(12): 812-8.

Moosmyayer, D., Dubel, S., Brocks, B., Watzka, H., Hampp, C., Scheurich, P., Little, M., m Pfizenmaier, K. (1995) A single-chain TNF receptor antagonist is an effective inhibitor of TNF mediated cytotoxicity. *Theraepeutic Immunoloqy* 2(1): 31-40.

Tracey, D., Klareskog, L., Sasso, E. H., Salfeld, J G. And Tak, P. P. (2008) Tumor necrosis factor antagonist mechanisms of action: A comprehensive review. *Pharmacology & Therapeutics.* 117: 244-279.

The invention claimed is:

1. A method for reducing post-operative cognitive dysfunction (POCD) in a patient as a result of performing a surgical procedure on the patient which comprises administering to the patient during the surgical procedure, a therapeutically effective amount of an anti-Human Tumor Necrosis Factor alpha monoclonal antibody which binds to, and blocks the action of, human TNF alpha so as to reduce POCD in the patient, wherein the monoclonal antibody is infliximab.

2. The method of claim 1, wherein the POCD is manifested as one or more of memory loss, memory impairment, concentration impairment, delirium, dementia and sickness behavior.

3. The method of claim 1, wherein the anti-Human TNF alpha monoclonal antibody is administered systemically.

4. The method of claim 3, wherein the anti-Human TNF alpha monoclonal antibody is administered intravenously.

5. The method of claim 1, wherein the anti-Human TNF alpha monoclonal antibody is administered by infusion.

6. The method of claim 1, wherein administration of the anti-Human TNFα monoclonal antibody to the patient commences just before the surgical procedure.

7. The method of claim 1, wherein the patient has delirium, Alzheimer's Disease, multiple sclerosis, stroke, Parkinson's Disease, Huntington's Disease, dementia, frontotemporal dementia, vascular dementia, HIV dementia, Post-Traumatic Stress Disorder, an infection, or Rheumatoid Arthritis.

8. The method of claim 1, wherein the surgical procedure is a cardiothoracic surgical procedure, an orthopedic surgical procedure, a neurological surgical procedure, a vascular surgical procedure, a plastic and reconstructive surgical procedure, a gynecological surgical procedure, an obstetric surgical procedure, a urological surgical procedure, a general surgical procedure, a head and neck surgical procedure, an ear, nose or throat (ENT) surgical procedure, a pediatric surgical procedure, a dental surgical procedure, a maxillofacial surgical procedure, an ophthalmic surgical procedure, a pain management surgical procedure, a trauma surgical procedure, or a minor surgical procedure.

9. The method of claim 8, wherein the surgical procedure is carried out under anesthesia.

10. The method of claim 1, wherein the patient is at risk for developing delirium as of the time of commencing administration of the anti-Human TNF alpha monoclonal antibody.

11. The method of claim 10, wherein the infliximab is administered by infusion in an amount between 2 and 10 mg per kg body weight of the patient.

12. The method of claim 11, wherein the amount is 5 mg per kg body weight of the patient.

13. The method of claim 9, wherein the anesthesia is general anesthesia, regional anesthesia, local anesthesia, sedation, or a combination of one or more of the preceding.

14. A method for reducing post-operative cognitive dysfunction (POCD) manifested as delirium in an elderly patient following an orthopedic surgical procedure which comprises administering infliximab to the patient by infusion commencing just before and during the surgical procedure in an amount between 2 and 10 mg per kg body weight of the patient.

15. A method of claim 14, wherein the amount is 5 mg per kg body weight of the patient.

* * * * *